US010947207B2

(12) United States Patent
Alam et al.

(10) Patent No.: US 10,947,207 B2
(45) Date of Patent: Mar. 16, 2021

(54) GP130 MODULATORS

(71) Applicant: THE REGENTS OF THE UNIVERSITY OF CALIFORNIA, Oakland, CA (US)

(72) Inventors: Mohammad Parvez Alam, Los Angeles, CA (US); Varghese John, Los Angeles, CA (US); Patricia Spilman, Mill Valley, CA (US); Kanagasabai Vadivel, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/323,033

(22) PCT Filed: Aug. 4, 2017

(86) PCT No.: PCT/US2017/045626
§ 371 (c)(1),
(2) Date: Feb. 4, 2019

(87) PCT Pub. No.: WO2018/027193
PCT Pub. Date: Feb. 8, 2018

(65) Prior Publication Data
US 2019/0292161 A1 Sep. 26, 2019

Related U.S. Application Data

(60) Provisional application No. 62/371,556, filed on Aug. 5, 2016.

(51) Int. Cl.
*C07D 277/42* (2006.01)
*C07D 263/48* (2006.01)
*C07D 413/04* (2006.01)
*C07D 417/04* (2006.01)
*C07D 487/08* (2006.01)
*C07D 263/28* (2006.01)
*A61K 31/4439* (2006.01)
*A61K 31/421* (2006.01)
*A61K 31/506* (2006.01)
*A61K 31/426* (2006.01)
*A61P 25/00* (2006.01)

(52) U.S. Cl.
CPC .......... *C07D 277/42* (2013.01); *A61K 31/421* (2013.01); *A61K 31/426* (2013.01); *A61K 31/4439* (2013.01); *A61K 31/506* (2013.01); *A61P 25/00* (2018.01); *C07D 263/28* (2013.01); *C07D 263/48* (2013.01); *C07D 413/04* (2013.01); *C07D 417/04* (2013.01); *C07D 487/08* (2013.01)

(58) Field of Classification Search
CPC .. C07D 277/42; C07D 263/28; C07D 487/08; C07D 417/04; C07D 413/04; C07D 263/48; A61P 25/00; A61K 31/506; A61K 31/421; A61K 31/4439; A61K 31/426
See application file for complete search history.

(56) References Cited

U.S. PATENT DOCUMENTS

| 7,067,507 B2 * | 6/2006 | Pulley ................. C07D 273/02 514/183 |
| 2005/0176789 A1 | 8/2005 | Hadida Ruah et al. |
| 2011/0112073 A1 * | 5/2011 | Thiele ................. A61K 31/415 514/217.04 |

FOREIGN PATENT DOCUMENTS

| WO | WO-2011/047129 A1 | 4/2011 |
| WO | WO-2012/064715 A1 | 5/2011 |
| WO | WO-2013/033037 A2 | 3/2013 |
| WO | WO-2013/033037 A3 | 3/2013 |
| WO | WO-2016/138533 A2 | 9/2016 |
| WO | WO-2016/138533 A3 | 9/2016 |

OTHER PUBLICATIONS

Singh, K., "Synthesis, characterization and antimicrobial study of some novel fluorine based 2-anninothiazoles." Int. J. Pharm. Pharm. Sci 6.10 (2014): 429-433.*
Hashimoto, Y., "Humanin inhibits neuronal cell death by interacting with a cytokine receptor complex or complexes involving CNTF receptor α/WSX-1/gp130." Molecular biology of the cell 20.12 (2009): 2864-2873.*
Xu, S., "Discovery of a novel orally active small-molecule gp130 inhibitor for the treatment of ovarian cancer." Molecular cancer therapeutics 12.6 (2013): 937-949.*
Akasofu, S., "Study of neuroprotection of donepezil, a therapy for Alzheimer's disease." Chemico-biological interactions 175.1-3 (2008): 222-226.*
MedLinePlus "Degenerative Nerve Diseases." 2014. Available from: http://www.nlm.nih.gov/medlineplus/degenerativenervediseases.html.*
Alzheimer's Disease Prevention WebMD (2005-2019)—7 Tips to Lower Your Risk of Getting Alzheimer's Disease (https://www.webmd.com/alzheimers/guide/understanding-alzheimers-disease-prevention#1), p. 1-11.*
Alam, M.P. et al. (Mar. 21, 2018, e-published Dec. 6, 2017). "A Small Molecule Mimetic of the Humanin Peptide as a Candidate for Modulating NMDA-Induced Neurotoxicity," ACS Chem Neuroscience 9(3):462-468.

(Continued)

Primary Examiner — John M Mauro
(74) Attorney, Agent, or Firm — Mintz, Levin, Cohn, Ferris, Glovsky and Popeo, P.C.

(57) ABSTRACT

There are provided, inter alia, compounds and methods useful for the treatment of neurological conditions, such as neurological disorders and neurodegenerative diseases, including Alzheimer's Disease.

17 Claims, 13 Drawing Sheets
Specification includes a Sequence Listing.

(56) References Cited

OTHER PUBLICATIONS

Extended European Search Report dated Mar. 19, 2020, for EP Patent Application No. 17837802.2, 12 pages.
Madhav, B. et al. (Apr. 21, 2012). "A tandem one-pot aqueous phase synthesis of thiazoles/selenazoles," Tetrahedron Letters 53:3835-3838.
Makam, P. et al. (Nov. 24, 2014, e-published Sep. 30, 2014). "2-Aminothiazole derivatives as antimycobacterial agents: Synthesis, characterization, in vitro and in silico studies," Eur J Med Chem 87:643-656.
International Search Report dated Nov. 28, 2017, for PCT Application No. PCT/US2017/045626, filed Aug. 4, 2017, 4 pages.
PUBCHEM Compound Database SID 53654661, available date: Sep. 12, 2008, retrieved Nov. 6, 2017, located at https://pubchem.ncbi.nlm.nih.gov/substance/53654661#section=Top, 5 pages.
PUBCHEM Compound Database SID 229788748, available date: Feb. 12, 2015, retrieved Sep. 6, 2017, located at https://pubchem.ncbi.nlm.nih.gov/substance/229788748#sectio, 7 pages.
Written Opinion dated Nov. 28, 2017 for PCT Application No. PCT/US2017/045626, filed Aug. 4, 2017, 8 pages.

\* cited by examiner

GP130 MODULATORS

CROSS-REFERENCE TO RELATED APPLICATIONS

This application is a Section 371 US national phase of International Application No. PCT/US2017/045626 filed Aug. 4, 2017, which claims the benefit of priority to U.S. Provisional Application No. 62/371,556, filed Aug. 5, 2016, which is hereby incorporated by reference in its entirety for all purposes.

BACKGROUND

Alzheimer's disease (AD) is the most prevalent age-related dementia. Currently approved therapeutics, however, provide only temporary symptomatic relief. Therefore a new approach to therapeutic development is urgently needed.

Provided herein inter alia are compounds and methods useful for these problems.

SUMMARY

In an aspect, there is provided a method for treating a neurological condition in a subject in need thereof, the method comprising administering to the subject a compound having a structure of Formula (I):

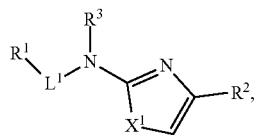
(I)

a pharmaceutically acceptable salt thereof. $X^1$ is S, Se or O. $L^1$ is $C_1$-$C_{10}$ unsubstituted alkyl or a bond. $R^1$ is hydrogen, halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $R^2$ and $R^3$ are independently hydrogen, halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

In another aspect, there is provided a compound having the structure of Formula (II):

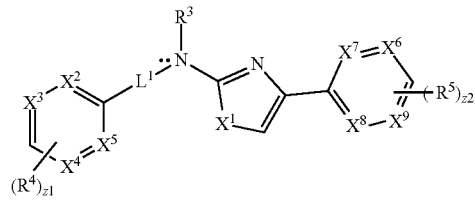
(II)

$R^4$ and $R^5$ are independently halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $X^2$, $X^3$, $X^4$, $X^5$, $X^6$, $X^7$, $X^8$ and $X^9$ are independently CH or N. The integers z1 and z2 are independently an integer from 0 to 5. $L^1$ is unsubstituted $C_1$-$C_{10}$ alkyl or a bond. $X^1$ is S, Se or O. In embodiments, $X^1$ is S or O. In embodiments, $X^1$ is S. In embodiments, $X^1$ is O. $R^3$ is hydrogen, halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. In embodiments, $R^3$ is hydrogen.

In another aspect, there is provided a compound having the structure of Formula (III):

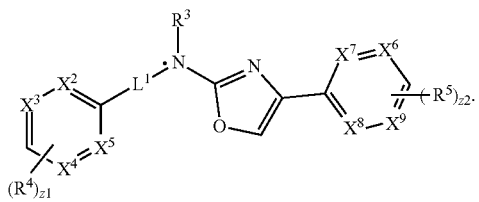
(III)

$R^4$ and $R^5$ are independently halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $X^2$, $X^3$, $X^4$, $X^5$, $X^6$, $X^7$, $X^8$ and $X^9$ are independently CH or N. The integers z1 and z2 are independently an integer from 0 to 5. $L^1$ is a bond or unsubstituted $C_1$-$C_{10}$ alkyl. $R^3$ is hydrogen, halogen, —$CF_3$, —$CCl_3$, —$CBr_3$, —$CI_3$, —CN, —OH, $NH_2$, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. In embodiments, R³ is hydrogen.

In another aspect, there is provided a compound selected from the group consisting of:

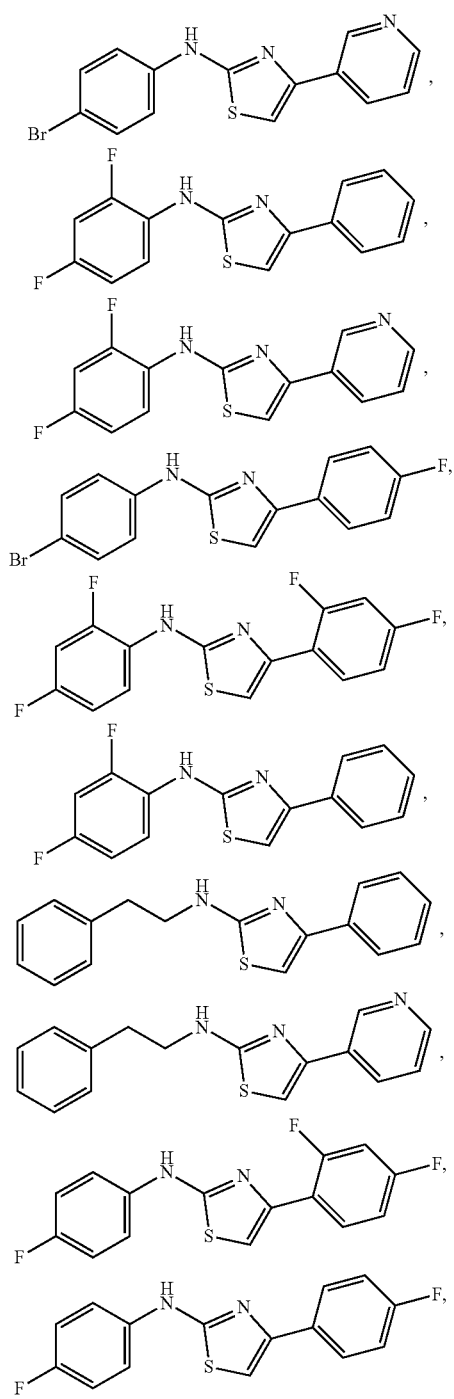

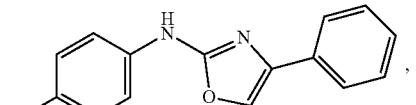

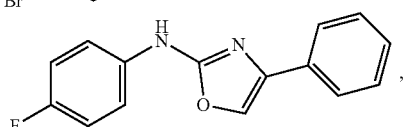

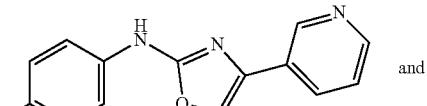
and

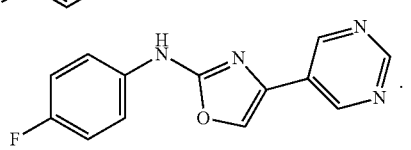

In another aspect, pharmaceutical compositions are provided comprising a compound disclosed herein, such as the compound of Formula I, Formula II and/or Formula III including all embodiments thereof, and one or more pharmaceutically acceptable excipients.

BRIEF DESCRIPTION OF THE DRAWINGS

FIG. 1A. HN, compound 2 and SC144 bind to the interface region between extracellular domains D4 and D5 of gp130. The extracellular domains D4-D6 of gp130 and HN (light gray) are shown in cartoon representation. Compound 2 (dark gray) and SC144 (white) are shown in stick representation. FIG. 1B. Molecular surface representation of the gp130 extracellular domains D4-D6 are shown with their electrostatic potential. The gp130 residues involved in interaction with the compound 2 (dark gray) and HN (light gray) are shown in FIGS. 1C and 1D, respectively. The residues within 5 Å radius of compound 2 or HN are shown. Carbon atoms in the gp130 D4 and D5 domains are shown in light gray.

(FIG. 16A) Control (DMSO-only) density is shown. (FIG. 16B) A clear reduction of neuronal density is seen as a result of NMDA-induced toxicity. (FIG. 16C) With MK801 pretreatment, the density of NMDA-treated neurons was similar to the DMSO-only control. (FIG. 16D) Pretreatment with compound 2 also prevented NMDA-induced toxicity and the density of living neurons was similar to DMSO-only control.

DETAILED DESCRIPTION

Definitions

Figures 1A, 1B, 1C, 1D:
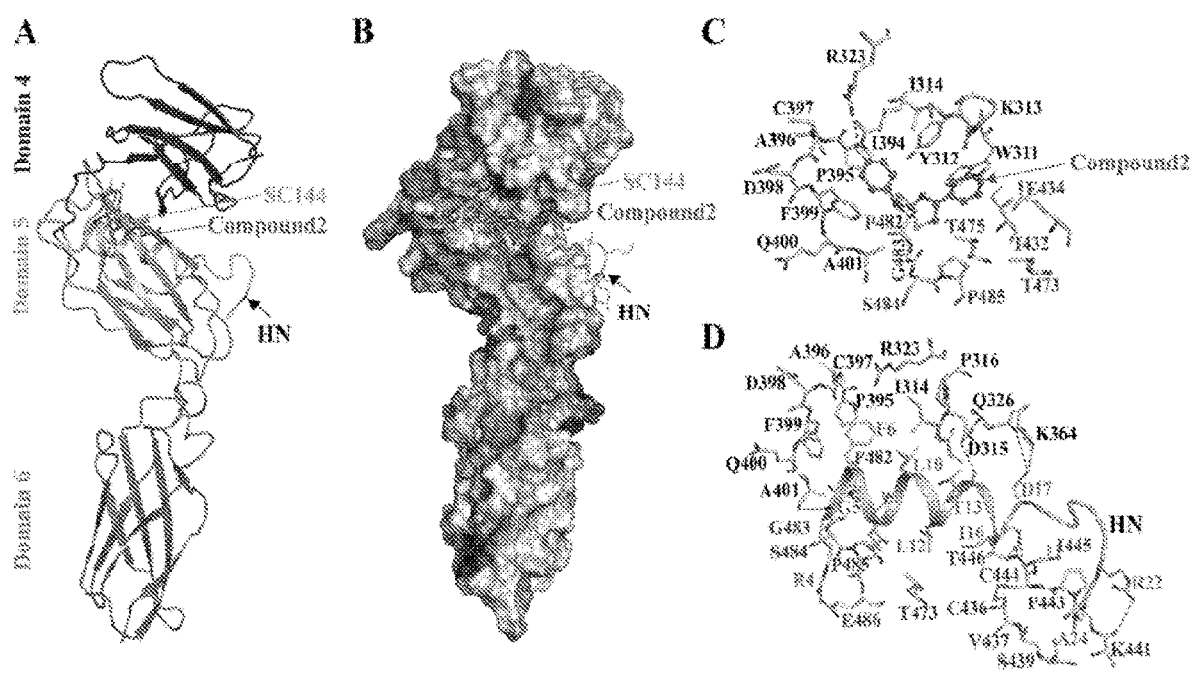
FIGS. 1A-1D. Binding site for humanin (HN), compound 2 and SC144 in the extracellular domains D4-D6 of gp130.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, and may have a number of carbon atoms designated (e.g. C$_1$-C$_{10}$ means one to ten carbons). Alkyl is not cyclized. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom (e.g. selected from the group consisting of O, N, P, S, Se and Si, and wherein the nitrogen, selenium, and sulfur atoms may optionally be oxidized, and the nitrogen heteroatom may optionally be quaternized). Heteroalkyl is not cyclized. The heteroatom(s) O, N, P, S, Se, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, —CH═CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SeR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (e.g. 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms (e.g. N, O, or S), wherein sulfur heteroatoms are optionally oxidized, and the nitrogen heteroatoms are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

The term "oxy" as used herein, alone or in combination, refers to —O—.

The term "aryloxy" as used herein, alone or in combination, refers to a substituted or unsubstituted aryl group attached to the parent molecular moiety through an oxy i.e. an ether group. An example of an unsubstituted aryl ether group is phenoxy (i.e., $C_6H_5O$—).

The term "heteroaryloxy" as used herein, alone or in combination, refers to a substituted or unsubstituted heteroaryl group attached to the parent molecular moiety through an oxy i.e. a heteroaryl ether group. An example of an unsubstituted heteroaryl ether group is thiophenyl (i.e., $C_6H_5SO$—).

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR" ", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the disclosure includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the disclosure includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), selenium (Se) and silicon (Si).

A "substituent group," as used herein, means a group selected from the following moieties:

(A) —OH, —NH$_2$, —CONH$_2$, —COOH, —SH, —CN, —CF$_3$, —NO$_2$, oxo, halogen, —N$_3$, —CCl$_3$, —CBr$_3$, —CI$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —CONH$_2$, —COOH, —SH, —CN, —CF$_3$, —NO$_2$, halogen, —N$_3$, —CCl$_3$, —CBr$_3$, —CI$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —CONH$_2$, —COOH, —SH, —CN, —CF$_3$, —NO$_2$, halogen, —N$_3$, —CCl$_3$, —CBr$_3$, —CI$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —CONH$_2$, —COOH, —SH, —CN, —CF$_3$, —NO$_2$, halogen, —N$_3$, —CCl$_3$, —CBr$_3$, —CI$_3$, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_5$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "isomer" or "isomers" as used herein, refer to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

The terms "analog" and "analogue", as used interchangeably herein and in accordance with their plain ordinary meaning within Chemistry and Biology, refer to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound.

The term "about" in the context of a numerical value means, unless indicated otherwise, the nominal numerical value+10% thereof.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

The symbol "⌇" denotes the point of attachment of a chemical moiety to the remainder of a molecule or chemical formula.

The term "about" in the context of a numerical value means, unless indicated otherwise, the nominal numerical value±10% thereof.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted."

Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished for example as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

Description of compounds of the present disclosure is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

A "nitrile" refers to a organic compound having a —CN group.

A "protected secondary amine" refers to the covalent attachment of a monovalent chemical moiety to an amine nitrogen atom that functions to prevent the amine moiety from reacting with reagents used in the chemical synthetic methods described herein (commonly referred to as "protecting" the amine group) and may be removed under conditions that do not substantially degrade the molecule of which the amine moiety forms a part (commonly referred to as "deprotecting" the amine group) thereby yielding a free amine. An amine protecting group can be acid labile, base labile, or labile in the presence of other reagents. Amine protecting groups include but are not limited to: -carbamates (such as -carbobenzyloxy (Cbz), -t-butoxycarbonyl (t-Boc), -fluorenylmethyloxycarbonyl (Fmoc), and -allyl carbamates), -benzyl, -4-methoxyphenyl, or -2,4-dimethoxyphenyl.

In some embodiments, the compound is a chemical species set forth herein.

The terms "contacting" and "reacting" are used synonymously herein in accordance with their plain ordinary meaning, and refer to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture. For example, two species may be a compound as described herein and a protein or enzyme. In some embodiments contacting includes allowing a compound described herein to interact with a protein or enzyme that is involved in a signaling pathway.

As used herein, "biomolecule" is used in its customary sense and refers to a molecule that is present in living organisms and synthetic derivatives thereof, including macromolecules such as proteins, carbohydrates, lipids, and nucleic acids, as well as small molecules such as primary metabolites, secondary metabolites, and natural products. A biomolecule includes but is not limited to nucleic acids (e.g. DNA and RNA), peptide nucleic acids, sugars, peptides, proteins, antibodies, lipids, small molecule affinity ligands e.g. inhibitors, biotin and haptens.

The term "agonize" or synonym thereof as used herein, refers, in the usual and customary sense, to an increase of activity of a biomolecule or complex of biomolecules, e.g., increase in Gp130 activity.

The term "antagonize" or synonym thereof as used herein, refers, in the usual and customary sense, to a decrease of activity, e.g., decrease in Gp130 activity.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present disclosure provides compounds, which are in a prodrug form. Prodrugs of the compounds described herein include those compounds that readily undergo chemical or enzymatic changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

As used herein, the term "salt" refers to acid or base salts of the compounds used in the methods of the present disclosure. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The terms "treating", or "treatment" refer to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; or improving a patient's physical or mental well-being. The treatment or amelioration of symptoms can be based on objective or subjective parameters, including the results of a physical examination, neuropsychiatric exams, and/or a psychiatric evaluation.

An "effective amount" is an amount sufficient to accomplish a stated purpose (e.g. achieve the effect for which it is administered, treat a disease, reduce enzyme activity, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present disclosure should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is the measurement of the activity of a protein in the absence of a compound as described herein (including embodiments and examples).

As defined herein, the term "activation," "activate," "activating" and the like in reference to a protein-activator interaction means positively affecting (e.g. increasing) the activity or function of the protein relative to the activity or function of the protein in the absence of the activator. Activation may refer to reduction of a disease or symptoms of disease. Activation may refer to an increase in the activity of a particular protein or nucleic acid target. The protein may be Gp130. Thus, activation includes, at least in part, partially or totally increasing stimulation, increasing, promoting, or expediting activation, or activating, sensitizing, or up-regulating signal transduction or enzymatic activity or the amount of a protein.

The term "modulator" refers to a composition that increases or decreases the level of a target molecule or the function of a target molecule or the physical state of the target of the molecule relative to the absence of the modulator.

The term "modulating" in the context of biological activity of a biomolecule, "modulating the activity" or the like refer, in the usual and customary sense, to increasing or decreasing the activity of the biomolecule (e.g., Gp130 receptor) relative to the absence of a modulating signal.

The term "modulate" in the context of biological activity of a biomolecule is used in accordance with its plain ordinary meaning and refers to the act of changing or varying one or more properties of a biomolecule relative to the absence of a modulating signal. "Modulation" in the context of biological activity refers to the process of changing or varying one or more properties of a biomolecule relative to the absence of a modulating signal. For example, a modulator of a target protein changes by increasing or decreasing a property or function of the target molecule or the amount of the target molecule. A modulator of a disease decreases a symptom, cause, or characteristic of the targeted disease.

"Selective" or "selectivity" or the like of a compound refers to the compound's ability to discriminate between molecular targets. "Specific", "specifically", "specificity", or the like of a compound refers to the compound's ability to cause a particular action, such as inhibition, to a particular molecular target with minimal or no action to other proteins in the cell.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

The terms "co-administer" and "co-administering" as used herein, refer to a compound described herein administered simultaneously, prior to, or following the administration of one or more additional compounds useful for treating neurological conditions as described herein. The compounds described herein can be administered alone or can be co-administered to a patient. Co-administration is meant to include simultaneous or sequential administration of the compound individually or in combination (more than one compound or agent). Thus, the preparations can also be combined, when desired, with other compounds for treating neurological conditions.

Co-administration includes administering a compound of the present disclosure within 0.5, 1, 2, 4, 6, 8, 10, 12, 16, 20, or 24 hours of a second compound useful for treating neurological conditions. Also contemplated herein, are embodiments, where co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. Co-administration can be accomplished by co-formulation, i.e., preparing a single pharmaceutical composition including both active agents. In other embodiments, the active agents can be formulated separately. The active and/or adjunctive agents may be linked or conjugated to one another. The compounds described herein may be combined with treatments for neurological conditions.

The term "associated" or "associated with" in the context of a substance or substance activity or function associated with a disease means that the disease is caused by (in whole or in part), a symptom of the disease is caused by (in whole or in part) the substance or substance activity or function, or a side-effect of the compound (e.g. toxicity) is caused by (in whole or in part) the substance or substance activity or function.

"Patient," "subject," "patient in need thereof," and "subject in need thereof" are herein used interchangeably and refer to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein. Disease as used herein refers to neurological conditions.

The term "linker" as used herein, refers to a divalent chemical group that covalently joins one chemical moiety to another.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" refers to a monovalent peptide.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and 0-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the disclosure.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the disclosure or individual domains of the polypeptides of the disclosure), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present disclosure includes polypeptides that are substantially identical to SEQ ID NO: 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

An example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision. Stable expression of a transfected gene can further be accomplished by infecting a cell with a lentiviral vector, which after infection forms part of (integrates into) the cellular genome thereby resulting in stable expression of the gene.

The terms "plasmid", "vector" or "expression vector" refer to a nucleic acid molecule that encodes for genes and/or regulatory elements necessary for the expression of genes. Expression of a gene from a plasmid can occur in cis or in trans. If a gene is expressed in cis, the gene and the regulatory elements are encoded by the same plasmid. Expression in trans refers to the instance where the gene and the regulatory elements are encoded by separate plasmids.

The terms "transfection", "transduction", "transfecting" or "transducing" can be used interchangeably and are defined as a process of introducing a nucleic acid molecule or a protein to a cell. Nucleic acids are introduced to a cell using non-viral or viral-based methods. The nucleic acid molecules may be gene sequences encoding complete proteins or functional portions thereof. Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art. The terms "transfection" or "transduction" also refer to introducing proteins into a cell from the external environment. Typically, transduction or transfection of a protein relies on attachment of a peptide or protein capable of crossing the cell membrane to the protein of interest. See, e.g., Ford et al. (2001) *Gene Therapy* 8:1-4 and Prochiantz (2007) *Nat. Methods* 4:119-20.

A "ligand" refers to an agent, e.g., a polypeptide or other molecule, capable of binding to a receptor.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The terms "Gp130 receptor," "Gp130," Gp130 protein," "IL6ST receptor," "IL6ST" or "IL6ST protein" as used herein interchangeably and according to their common, ordinary meaning (e.g., transmembrane protein "glycoprotein 130"), refer to proteins of the same or similar names and functional fragments and homologs thereof. The terms include any recombinant or naturally occurring form of, or variants thereof that maintain Gp130 activity (e.g. within at least 30%, 40%, 50%, 60%, 70%, 80%, 90%, 95%, or 100% activity compared to Gp130). In embodiments, the Gp 130 receptor has at least 80%, 85%, 90%, 95%, 96%, 97%, 98%, 99% or 100% sequence identity to SEQ ID NO: 1 or a functional fragment thereof (e.g. 700 contiguous amino acids of SEQ ID NO: 1, 750 contiguous amino acids of SEQ ID NO: 1, 800 contiguous amino acids of SEQ ID NO: 1, 850 contiguous amino acids of SEQ ID NO: 1, 870 contiguous amino acids of SEQ ID NO: 1, 880 contiguous amino acids of SEQ ID NO: 1, 890 contiguous amino acids of SEQ ID NO: 1, 900 contiguous amino acids of SEQ ID NO: lor 910 contiguous amino acids of SEQ ID NO: 1. (see http://www.uniprot.org/uniprot/P40189).

The Gp130 receptor comprises six extracellular domains: an immunoglobulin-like C2-type domain (referred to as "binding domain 1" or "D1"); fibronectin type-III-1 (referred to herein as "binding domain 2" or "D2"); fibronectin type-III-2 (referred to herein as "binding domain 3" or "D3"); fibronectin type-III-3 (referred to herein as "binding domain 4" or "D4"); fibronectin type-III-4 (referred to as "binding domain 5" or "D5"); and fibronectin type-III-5 (referred to as "binding domain 6" or "D6").

The compounds of the present disclosure are specifically designed to fit within a binding site of the Gp130 receptor and make contact with amino acids residing on the surface of the binding site of the Gp130 receptor. In embodiments, the compounds according to the disclosure provided herein, selectively bind to one or more binding sites of the Gp130 receptor as described herein.

The terms "binding domain 4", "domain 4" and "D4", as used interchangeably herein, refer to amino acid residues 307-402 of SEQ. ID NO. 1.

The terms "binding domain 5", "domain 5" and "D5", as used interchangeably herein, refer to amino acid residues 307-402 of SEQ. ID NO. 1.

In embodiments, the compounds of the present disclosure bind to amino acid residues 311-317 (Trp-Tyr-Lys-Ile-Asp-Pro-Ser), 322-325 (Tyr-Arg-Thr-Val), 371-373 (Asn-Asp-Arg) and 393-401 (Thr-Ile-Pro-Ala-Cys-Asp-Phe-Gln-Ala) of binding domain 4, and are capable of binding to the interface region between binding domain 3 and binding domain 4 and/or between binding domain 4 and binding domain 5.

In embodiments, the compounds of the present disclosure bind to amino acid residues 431-433 (Tyr-Ile-Leu), 445-447 (Ile-Thr-Asp), 472-477 (Ile-Thr-Val-Thr-Pro-Val) and 481-486 (Gly-Pro-Gly-Ser-Pro-Glu) of binding domain 5 (D5), and are capable of binding to the interface region between binding domain 4 and binding domain 5 and/or between binding domain 5 and binding domain 6.

In embodiments, the compounds of the present disclosure bind to the amino acid residues 311-317 (Trp-Tyr-Lys-Ile-Asp-Pro-Ser), 322-325 (Tyr-Arg-Thr-Val), 371-373 (Asn-Asp-Arg) and 393-401 (Thr-Ile-Pro-Ala-Cys-Asp-Phe-Gln-Ala) of binding domain 4 (D4) and the amino acid residues 431-433 (Tyr-Ile-Leu), 445-447 (Ile-Thr-Asp), 472-477 (Ile-Thr-Val-Thr-Pro-Val) and 481-486 (Gly-Pro-Gly-Ser-Pro-Glu) of binding domain 5, and are capable of binding to the interface region between binding domain 4 and binding domain 5 and/or between binding domain 3 and binding domain 4 and/or between binding domain 5 and binding domain 6.

A "Gp130 receptor agonist" as used herein, refers to a compound (e.g. a biomolecule or synthetic chemical molecule (e.g. a small molecule) capable of binding to binding site of the Gp130 receptor and increasing Gp130 activity or function.

The terms "humanin" and "HN" as used interchangeably herein, refer in the usual and customary sense, to the peptide encoded in the mitochondrial genome by the gene MT-RNR2. It is observed that production of humanin inside of the mitochondria affords a 21-residue polypeptide, whereas production in the cytosol affords a 24-residue polypeptide. See e.g., Hashimoto, Y., et al., 2001, *Proc. Natl. Acad. Sci. USA* 98:6336-6341; Guo, B., et al., 2003, *Nature* 423:456-461; Ikonen, M., 2003, *Proc. Natl. Acad. Sci. USA* 100: 13042-13047. Humanin binds to amino acid residues 311-316 (Trp-Tyr-Lys-Ile-Asp-Pro), 323-326 (Arg-Thr-Val-Gln), 364 (Lys), 395-402 (Pro-Ala-Cys-Asp-Phe-Gln-Ala-Thr) of Gp130 Domain 4, and to amino acid residues 434-447 (Glu-Trp-Cys-Val-Leu-Ser-Asp-Lys-Ala-Pro-Cys-Ile-Thr-Asp-Trp), 463 (Asn), 468 (Lys), 471 (Leu), 473 (Thr), 477 (Val), and 482-487 (Pro-Gly-Ser-Pro-Glu-Ser-Ile).

The terms "N-methyl-D-aspartate receptor", "NMDA receptor" and "NMDAR", as used interchangeably herein, refer to a glutamate receptor and ion channel protein found in neurons. The NMDA receptor is an ionotropic receptor activated when glutamate and glycine (or D-serine) bind to it, and when activated it allows positively charged ions to flow through the cell membrane. The NMDA receptor controls synaptic plasticity and memory function. The agonist molecule N-methyl-D-aspartate (NMDA) binds selectively to the NMDA receptor but not to other glutamate receptors.

The term "neurodegeneration" as used herein, refers to the progressive loss of structure or function of neurons, including death of neurons.

The term "neuron" or "neurons" as used herein, refers to the building blocks of the nervous system which includes the brain and spinal cord. A neuron, also known as a neurone or nerve cell, is an electrically excitable cell that processes and transmits information through electrical and chemical signals. These signals between neurons occur via specialized connections called synapses. Neurons can connect to each other to form neural networks. Neurons are major components of the brain and spinal cord of the central nervous system (CNS), and of the autonomic gangliaof the peripheral nervous system. There are several types of specialized neurons. Sensory neurons respond to stimuli such as touch, sound or light and all other stimuli affecting the cells of the sensory organs that then send signals to the spinal cord and brain. Motor neurons receive signals from the brain and spinal cord to cause muscle contractions and affect glandular outputs. Interneurons connect neurons to other neurons within the same region of the brain, or spinal cord in neural networks.

The terms "neurological condition" and "neurological conditions", as used interchangeably herein, refer in the usual and customary sense, to "neurodegenerative disease", "neurodegenerative diseases", "neurological disorder" and "neurological disorders".

The terms "neurodegenerative disease", "neurodegenerative diseases", "neurological disorder" and "neurological disorders" as used interchangeably herein, refer in the usual and customary sense, to a range of conditions which primarily affect the neurons in the human brain and/or spinal cord, including but not limited to, Alzheimer's Disease, Amyotrophic Lateral Sclerosis, Friedreich's Ataxia, Huntington's Disease, Lewy Body Disease, Parkinson's Disease, Spinal Muscular Atrophy, Alpers' Disease, Batten Disease, Cerbro-Oculo-Facio Skeletal Syndrome, Corticobasal Degeneration, Gerstmann-Straussler-Scheinker Disease, Kuru, Leigh's Disease, Monomelic Amyotrophy, Multiple System Atrophy, Shy-Drager Syndrome, Neurodegeneration with Brain Iron Accumulation, Opsoclonus Myoclonus, Prion Disease, Progressive Multifocal Leukoencephalpathy and Striatonigral Degeneration, traumatic brain injury (TBI), stroke, intracellular hemorrhage and ischemia and reperfusion injury (see, Wang T, Zhang L, et. al., [Gly14] Humanin reduces histopathology and improves functional outcome after TBI, Neuroscience 23170-23181 (2013); Want T, Huang Y et al. Humanin offers neuroprotection . . . intracerebral hemorrhage. Behav. Brain Res 247, 132-139 (2013); Zhao S T, Huang X T et al., Humanin protects cortical neurons from ischemia and reperfusion injury . . . Neuro Chem Res 37 (1), 153-160, 2012; and Zhao S T, Huang X T et al., Humanin protects cortical neurons from ischemia and reperfusion injury . . . Neuro Chem Res 37 (1), 153-160, 2012), epilepsy, seizures associated with epilepsy, seizures associated with neurological conditions, and cerebrovascular dementia through inhibition of Abeta-mediated cell death of human cerebrovascular smooth muscle cells (see, Jung S S, Van Nostrand W E, Humanin rescues human cerebrovascular smooth muscle cells from Abeta-induced toxicity, J Neurochem 84 (2) 266-272, 2003).

The term "Alzheimer's disease," "AD" or the like refer, in the usual and customary sense, to a chronic neurodegenerative disease, which is understood to account for about 60%-70% of cases of dementia. Without wishing to be bound by theory, it is postulated that the deposition of extracellular amyloid beta (AP3) is the fundamental cause for AD.

Methods

In an aspect, there is provided a method for treating a neurological condition in a subject in need thereof, the method comprising administering to the subject a compound having a structure of Formula (I):

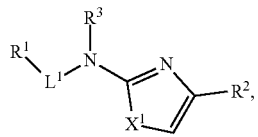

(I)

or a pharmaceutically acceptable salt thereof. $X^1$ is S, Se or O. $L^1$ is $C_1$-$C_{10}$ unsubstituted alkyl or a bond. $R^1$ is hydrogen, halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $R^2$ and $R^3$ are independently hydrogen, halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

In embodiments, $X^1$ is S. In embodiments, $X^1$ is O. In embodiments, $X^1$ is Se. In embodiments, $L^1$ is unsubstituted $C_1$-$C_{10}$ alkyl. In embodiments, $L^1$ is a bond. In embodiments, $R^3$ is hydrogen, methyl or substituted or unsubstituted cyclopropyl. In embodiments, $R^3$ is hydrogen. In embodiments, $R^1$ is substituted or unsubstituted aryl or substituted or unsubstituted heteroaryl. In embodiments, $R^1$ is substituted or unsubstituted heteroaryl. In embodiments, $R^1$ is substituted or unsubstituted pyridinyl or substituted or unsubstituted pyrimidinyl. In embodiments, $R^1$ is substituted or unsubstituted aryl. In embodiments, $R^1$ is substituted or unsubstituted phenyl. In embodiments, $R^2$ is substituted or unsubstituted aryl or substituted or unsubstituted heteroaryl. In embodiments, $R^2$ is substituted or unsubstituted aryl. In embodiments, $R^2$ is substituted or unsubstituted phenyl. In embodiments, $R^2$ is substituted or unsubstituted heteroaryl. In embodiments, $R^2$ is substituted or unsubstituted pyridinyl or substituted or unsubstituted pyrimidinyl. In embodiments, $R^1$ is substituted alkyl, substituted cycloalkyl, substituted heteroalkyl, substituted heterocycloalkyl, substituted aryl, or substituted heteroaryl (e.g., substituted with a substituent group, a size-limited substituent group, or lower substituent group).

In embodiments, $R^1$ is substituted alkyl substituted with a substituent group, a size-limited substituent group, or lower substituent group. In embodiments, $R^1$ is substituted cycloalkyl substituted with a substituent group, a size-limited substituent group, or lower substituent group. In embodiments, $R^1$ is substituted heteroalkyl substituted with a substituent group, a size-limited substituent group, or lower substituent group. In embodiments, $R^1$ is substituted heterocycloalkyl substituted with a substituent group, a size-limited substituent group, or lower substituent group. In embodiments, $R^1$ is substituted aryl substituted with a substituent group, a size-limited substituent group, or lower substituent group. In embodiments, $R^1$ is substituted heteroaryl substituted with a substituent group, a size-limited substituent group, or lower substituent group. In embodiments, $R^1$ is $R^{100}$-substituted or unsubstituted alkyl, $R^{100}$-substituted or unsubstituted heteroalkyl, $R^{100}$-substituted or unsubstituted cycloalkyl, $R^{100}$-substituted or unsubstituted heterocycloalkyl, $R^{100}$-substituted or unsubstituted aryl or $R^{100}$-substituted or unsubstituted heteroaryl. $R^{100}$ is independently halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{101}$-substituted or unsubstituted alkyl, $R^{100}$-substituted or unsubstituted heteroalkyl, $R^{100}$-substituted or unsubstituted cycloalkyl, $R^{100}$-substituted or unsubstituted heterocycloalkyl, $R^{100}$-substituted or unsubstituted aryl or $R^{100}$-substituted or unsubstituted heteroaryl. $R^{101}$ is independently halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl or unsubstituted heteroaryl. In embodiments, R$^1$ is unsubstituted alkyl, unsubstituted cycloalkyl, unsubstituted heteroalkyl, unsubstituted heterocycloalkyl, unsubstituted aryl, or unsubstituted heteroaryl.

In embodiments, R$^1$ is substituted aryl. In embodiments, R$^1$ is unsubstituted aryl. In embodiments, R$^1$ is substituted heteroaryl. In embodiments, R$^1$ is unsubstituted heteroaryl. In embodiments, R$^1$ is substituted pyridinyl. In embodiments, R$^1$ is unsubstituted pyridinyl. In embodiments, R$^1$ is substituted pyrimidinyl. In embodiments, R$^1$ is unsubstituted pyrimidinyl. In an embodiment, R$^1$ is substituted phenyl. In embodiments, R$^1$ is unsubstituted phenyl.

In embodiments, R$^2$ is substituted alkyl substituted with a substituent group, a size-limited substituent group, or lower substituent group. In embodiments, R$^2$ is substituted cycloalkyl substituted with a substituent group, a size-limited substituent group, or lower substituent group. In embodiments R$^2$ is substituted heteroalkyl substituted with a substituent group, a size-limited substituent group, or lower substituent group. In embodiments, R$^2$ is substituted heterocycloalkyl substituted with a substituent group, a size-limited substituent group, or lower substituent group. In embodiments, R$^2$ is substituted aryl substituted with a substituent group, a size-limited substituent group, or lower substituent group. In embodiments, R$^2$ is substituted heteroaryl substituted with a substituent group, a size-limited substituent group, or lower substituent group. In embodiments, R$^2$ is R$^{200}$ substituted or unsubstituted alkyl, R$^{200}$-substituted or unsubstituted heteroalkyl, R$^{200}$-substituted or unsubstituted cycloalkyl, R$^{200}$-substituted or unsubstituted heterocycloalkyl, R$^{200}$-substituted or unsubstituted aryl or R$^{200}$-substituted or unsubstituted heteroaryl. In embodiments, R$^{200}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{201}$-substituted or unsubstituted alkyl, R$^{201}$-substituted or unsubstituted heteroalkyl, R$^{201}$-substituted or unsubstituted cycloalkyl, R$^{201}$-substituted or unsubstituted heterocycloalkyl, R$^{201}$-substituted or unsubstituted aryl or R$^{201}$-substituted or unsubstituted heteroaryl. In embodiments, R$^{201}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl or unsubstituted heteroaryl. In embodiments, R$^2$ is unsubstituted alkyl, unsubstituted cycloalkyl, unsubstituted heteroalkyl, unsubstituted heterocycloalkyl, unsubstituted aryl, or unsubstituted heteroaryl.

In embodiments, R$^2$ is substituted aryl. In embodiments, R$^2$ is unsubstituted aryl. In embodiments, R$^2$ is substituted heteroaryl. In embodiments, R$^2$ is unsubstituted heteroaryl. In embodiments, R$^2$ is substituted phenyl. In embodiments, R$^2$ is unsubstituted phenyl. In embodiments, R$^2$ is substituted pyridinyl. In embodiments, R$^2$ is unsubstituted pyridinyl. In embodiments, R$^2$ is or substituted pyrimidinyl. In embodiments, R$^2$ is unsubstituted pyrimidinyl.

In embodiments, R$^3$ is substituted alkyl substituted with a substituent group, a size-limited substituent group, or lower substituent group. In embodiments, R$^3$ is substituted cycloalkyl substituted with a substituent group, a size-limited substituent group, or lower substituent group. In embodiments R$^3$ is substituted heteroalkyl substituted with a substituent group, a size-limited substituent group, or lower substituent group. In embodiments, R$^3$ is substituted heterocycloalkyl substituted with a substituent group, a size-limited substituent group, or lower substituent group. In embodiments, R$^3$ is substituted aryl substituted with a substituent group, a size-limited substituent group, or lower substituent group. In embodiments, R$^3$ is substituted heteroaryl substituted with a substituent group, a size-limited substituent group, or lower substituent group. In embodiments, R$^3$ is R$^{300}$ substituted or unsubstituted alkyl, R$^{300}$-substituted or unsubstituted heteroalkyl, R$^{300}$ substituted or unsubstituted cycloalkyl, R$^{300}$-substituted or unsubstituted heterocycloalkyl, R$^{300}$-substituted or unsubstituted aryl or R$^{300}$-substituted or unsubstituted heteroaryl. In embodiments, R$^{300}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{301}$-substituted or unsubstituted alkyl, R$^{301}$-substituted or unsubstituted heteroalkyl, R$^{301}$-substituted or unsubstituted cycloalkyl, R$^{301}$-substituted or unsubstituted heterocycloalkyl, R$^{301}$-substituted or unsubstituted aryl or R$^{301}$-substituted or unsubstituted heteroaryl. In embodiments, R$^{301}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl or unsubstituted heteroaryl. In embodiments, R$^3$ is unsubstituted alkyl, unsubstituted cycloalkyl, unsubstituted heteroalkyl, unsubstituted heterocycloalkyl, unsubstituted aryl, or unsubstituted heteroaryl.

In embodiments, R$^3$ is hydrogen. In embodiments, R$^3$ is unsubstituted alkyl. In embodiments, R$^3$ is unsubstituted C$_1$-C$_5$ alkyl. In embodiments, R$^3$ is methyl. In embodiments, R$^3$ is substituted cyclopropyl. In embodiments, R$^3$ is unsubstituted cyclopropyl.

In embodiments, the compound is the structure of Formula (II):

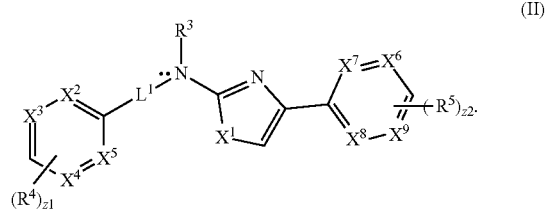

In Formula (II), $L^1$, $R^3$ and $X^1$ are as defined above, including embodiments thereof. $R^4$ and $R^5$ are independently halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $X^2$, $X^3$, $X^4$, $X^5$, $X^6$, $X^7$, $X^8$ and $X^9$ are independently CH or N. The integers z1 and z2 are independently an integer from 0 to 5. $L^1$ is unsubstituted $C_1$-$C_{10}$ alkyl or a bond. Where one or more of $X^2$, $X^3$, $X^4$ or $X^5$ are CH and $R^4$ is attached, it is understood that the hydrogen of the CH is replaced with the $R^4$ substituent in keeping with the normal rules of chemical valency. Where one or more of $X^2$, $X^3$, $X^4$ or $X^5$ are N, it us understood that N is not attached to $R^4$ in keeping with the normal rules of chemical valency. Where one or more of $X^6$, $X^7$, $X^8$ or $X^9$ are CH and $R^5$ is attached, it is understood that the hydrogen of the CH is replaced with the $R^5$ substituent in keeping with the normal rules of chemical valency. Where one or more of $X^6$, $X^7$, $X^8$ or $X^9$ are N, it us understood that N is not attached to $R^5$ in keeping with the normal rules of chemical valency.

In embodiments, the compound is the structure of Formula (IIA):

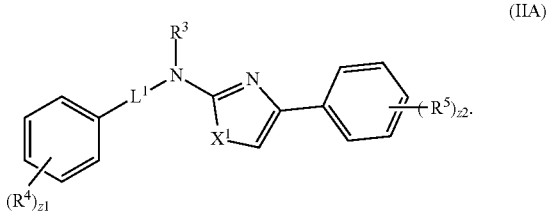

(IIA)

In Formula (IIA), z1, z2, $L^1$, $R^3$, $R^4$, $R^5$, and $X^1$ are as defined above, including embodiments thereof.

In embodiments, the compound is the structure of Formula (IIB):

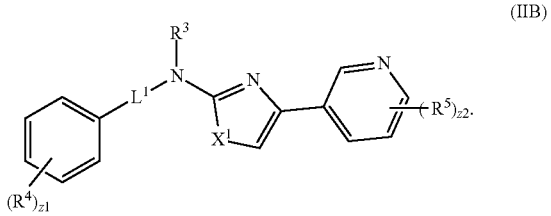

(IIB)

In embodiments, the compound is the structure of Formula (IIC). In Formula (IIB), z1, z2, $L^1$, $R^3$, $R^4$, $R^5$, and $X^1$ are as defined above, including embodiments thereof.

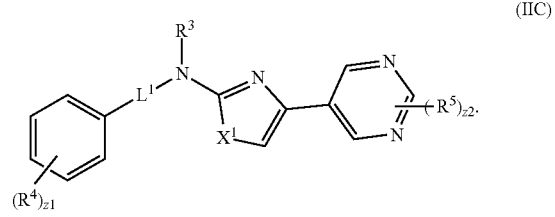

(IIC)

In Formula (IIC), z1, z2, $L^1$, $R^3$, $R^4$, $R^5$, and $X^1$ are as defined above, including embodiments thereof.

In embodiments, $R^4$ is substituted alkyl substituted with a substituent group, a size-limited substituent group, or lower substituent group. In embodiments, $R^4$ is substituted cycloalkyl substituted with a substituent group, a size-limited substituent group, or lower substituent group. In embodiments $R^4$ is independently substituted heteroalkyl substituted with a substituent group, a size-limited substituent group, or lower substituent group. In embodiments, $R^4$ is substituted heterocycloalkyl substituted with a substituent group, a size-limited substituent group, or lower substituent group. In embodiments, $R^4$ is substituted aryl substituted with a substituent group, a size-limited substituent group, or lower substituent group. In embodiments, $R^4$ is substituted heteroaryl substituted with a substituent group, a size-limited substituent group, or lower substituent group. In embodiments, $R^4$ is $R^{400}$-substituted or unsubstituted alkyl, $R^{400}$-substituted or unsubstituted heteroalkyl, $R^{400}$-substituted or unsubstituted cycloalkyl, $R^{400}$-substituted or unsubstituted heterocycloalkyl, $R^{400}$-substituted or unsubstituted aryl or $R^{400}$-substituted or unsubstituted heteroaryl. In embodiments, $R^{400}$ is halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{400}$-substituted or unsubstituted alkyl, $R^{400}$-substituted or unsubstituted heteroalkyl, $R^{400}$-substituted or unsubstituted cycloalkyl, $R^{400}$-substituted or unsubstituted heterocycloalkyl, $R^{400}$-substituted or unsubstituted aryl or $R^{400}$-substituted or unsubstituted heteroaryl. In embodiments, $R^{400}$ is halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, unsubstituted alkyl, unsubstituted heteroalkyl, unsubstituted cycloalkyl, unsubstituted heterocycloalkyl, unsubstituted aryl or unsubstituted heteroaryl. In embodiments, $R^4$ is unsubstituted alkyl, unsubstituted cycloalkyl, unsubstituted heteroalkyl, unsubstituted heterocycloalkyl, unsubstituted aryl, or unsubstituted heteroaryl.

In embodiments, $R^4$ is substituted alkyl substituted with a substituent group, a size-limited substituent group, or lower substituent group. In embodiments $R^4$ is independently substituted heteroalkyl substituted with a substituent group, a size-limited substituent group, or lower substituent group. In embodiments, $R^4$ is $R^{400}$-substituted or unsubstituted alkyl, $R^{400}$-substituted or unsubstituted heteroalkyl. In embodiments, $R^{400}$ is halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC (O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{400}$-substituted or unsubstituted alkyl, R$^{400}$-substituted or unsubstituted heteroalkyl. In embodiments, R$^{400}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl. In embodiments, R$^4$ is unsubstituted alkyl or unsubstituted heteroalkyl.

In embodiments, R$^4$ is halogen. In embodiments, R$^4$ is —F. In embodiments, R$^4$ is —Br. In embodiments, R$^4$ is unsubstituted alkyl. In embodiments, R$^4$ is unsubstituted C$_1$-C$_5$ alkyl. In embodiments, R$^4$ is halogen-substituted alkyl. In embodiments, R$^4$ is halogen-substituted C$_1$-C$_5$ alkyl. In embodiments, R$^4$ is unsubstituted heteroalkyl. In embodiments, R$^4$ is unsubstituted 2 to 5 membered heteroalkyl. In embodiments, R$^4$ is halogen-substituted heteroalkyl. In embodiments, R$^4$ is halogen-substituted 2 to 5 membered heteroalkyl. In embodiments, R$^4$ is methyl. In embodiments, R$^4$ is CF$_3$.

In embodiments, R$^5$ is substituted alkyl substituted with a substituent group, a size-limited substituent group, or lower substituent group. In embodiments, R$^5$ is substituted cycloalkyl substituted with a substituent group, a size-limited substituent group, or lower substituent group. In embodiments R$^5$ is substituted heteroalkyl substituted with a substituent group, a size-limited substituent group, or lower substituent group. In embodiments, R$^5$ is substituted heterocycloalkyl substituted with a substituent group, a size-limited substituent group, or lower substituent group. In embodiments, R$^4$ and R$^5$ are independently substituted aryl substituted with a substituent group, a size-limited substituent group, or lower substituent group. In embodiments, R$^5$ is substituted heteroaryl substituted with a substituent group, a size-limited substituent group, or lower substituent group. In embodiments, R$^5$ is R$^{500}$-substituted or unsubstituted alkyl, R$^{500}$-substituted or unsubstituted heteroalkyl, R$^{500}$-substituted or unsubstituted cycloalkyl, R$^{500}$-substituted or unsubstituted heterocycloalkyl, R$^{500}$-substituted or unsubstituted aryl or R$^{500}$-substituted or unsubstituted heteroaryl. In embodiments, R$^{500}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{500}$-substituted or unsubstituted alkyl, R$^{500}$-substituted or unsubstituted heteroalkyl, R$^{500}$-substituted or unsubstituted cycloalkyl, R$^{500}$-substituted or unsubstituted heterocycloalkyl, R$^{500}$-substituted or unsubstituted aryl or R$^{500}$-substituted or unsubstituted heteroaryl. In embodiments, R$^{500}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl or unsubstituted heteroaryl. In embodiments, R$^5$ is unsubstituted alkyl, unsubstituted cycloalkyl, unsubstituted heteroalkyl, unsubstituted heterocycloalkyl, unsubstituted aryl, or unsubstituted heteroaryl.

In embodiments, R$^5$ is substituted alkyl substituted with a substituent group, a size-limited substituent group, or lower substituent group. In embodiments R$^5$ is substituted heteroalkyl substituted with a substituent group, a size-limited substituent group, or lower substituent group. In embodiments, R$^5$ is R$^{500}$-substituted or unsubstituted alkyl, or R$^{500}$-substituted or unsubstituted heteroalkyl. In embodiments, R$^{500}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{500}$-substituted or unsubstituted alkyl, or R$^{500}$-substituted or unsubstituted heteroalkyl. In embodiments, R$^{500}$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, or unsubstituted heteroalkyl. In embodiments, R$^5$ is unsubstituted alkyl or unsubstituted heteroalkyl.

In embodiments, R$^5$ is halogen. In embodiments, R$^5$ is unsubstituted alkyl. In embodiments, R$^5$ is unsubstituted C$_1$-C$_5$ alkyl. In embodiments, R$^5$ is halogen-substituted alkyl. In embodiments, R$^5$ is halogen-substituted C$_1$-C$_5$ alkyl. In embodiments, R$^5$ is unsubstituted heteroalkyl. In embodiments, R$^5$ is unsubstituted 2 to 5 membered heteroalkyl. In embodiments, R$^5$ is halogen-substituted heteroalkyl. In embodiments, R$^5$ is halogen-substituted 2 to 5 membered heteroalkyl. In embodiments, R$^5$ is methyl. In embodiments, R$^5$ is CF$_3$.

In embodiments, if R$^4$ or R$^5$ are a methyl, the methyl is a deuterated methyl.

In embodiments, z1 and z2 are independently 0 or 1.

In embodiments, the compound is selected from the group consisting of:

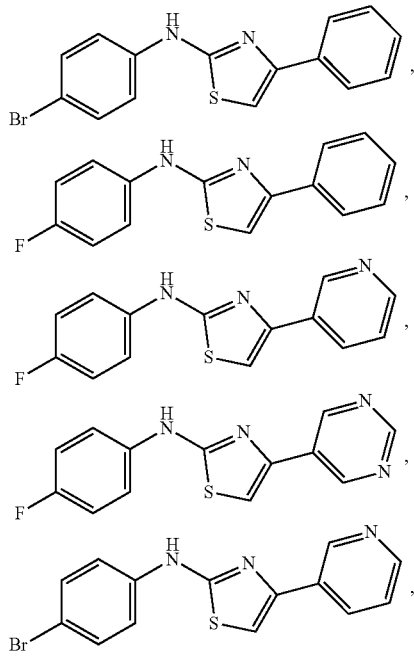

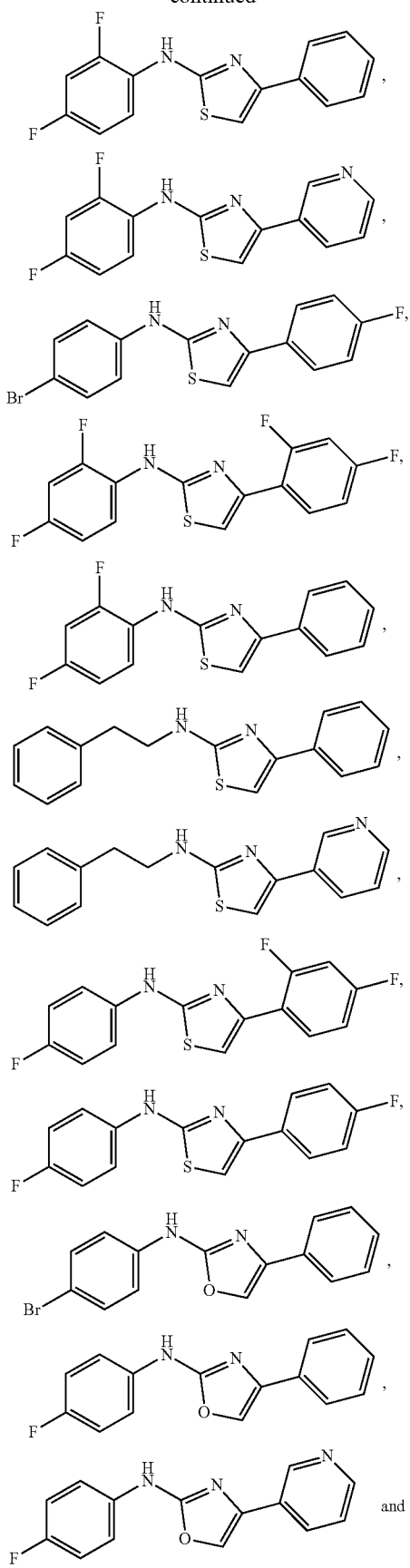

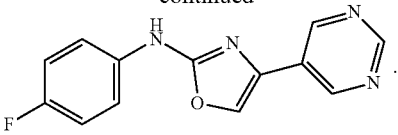

In embodiments, the neurological condition is a neurological disorder or a neurodegenerative disease selected from the group consisting of Alzheimer's Disease, Amyotrophic Lateral Sclerosis, Friedreich's Ataxia, Huntington's Disease, Lewy Body Disease, Parkinson's Disease, Spinal Muscular Atrophy, Alpers' Disease, Batten Disease, Cerbro-Oculo-Facio Skeletal Syndrome, Corticobasal Degeneration, Gerstmann-Straussler-Scheinker Disease, Kuru, Leigh's Disease, Monomelic Amyotrophy, Multiple System Atrophy, Shy-Drager Syndrome, Neurodegeneration with Brain Iron Accumulation, Opsoclonus Myoclonus, Prion Disease, Progressive Multifocal Leukoencephalpathy, Striatonigral Degeneration, traumatic brain injury (TBI), stroke, intracellular hemorrhage and ischemia and reperfussion injury, epilepsy, seizures associated with epilepsy, seizures associated with neurological conditions, and cerebrovascular dementia through inhibition of Abeta-mediated cell death of human cerebrovascular smooth muscle cells. In embodiments, the neurological condition is a neurological disorder. In embodiments, the neurological condition is a neurodegenerative disease. In embodiments, the neurological condition is Alzheimer's Disease.

In embodiments, the administering comprises contacting a compound as disclosed herein with a cell, wherein the cell comprises a Gp130 receptor, and wherein the compound is capable of binding to the Gp130 receptor. In embodiments, a compound as disclosed herein is capable of binding to binding domain 4 and binding domain 5 of the Gp130 receptor. In embodiments, a compound as disclosed herein is capable of binding to binding domain 4 of the Gp130 receptor. In embodiments, a compound as disclosed herein is capable of binding to binding domain 5 of the Gp130 receptor.

In embodiments, the cell is a human cell. In embodiments, the cell is a neuron.

In embodiments, the method comprises co-administering a compound as disclosed herein with a compound useful for treating neurological conditions. In embodiments, the compounds for treating neurological conditions as disclosed herein can be co-administered in a combined synergistic amount with one or more compounds useful for treating neurological conditions. A "combined synergistic amount" as used herein refers to the sum of a first amount (e.g., a compound disclosed herein) and a second amount (e.g., a compound for treating neurological conditions) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of compounds administered in combination where the measured effect is greater than the sum of the individual effects of each of the compounds administered alone as a single agent.

In another aspect, there is provided a method of increasing pSTAT3 expression in a cell. The method includes contacting a cell which includes a Gp130 receptor with a compound as disclosed herein, thereby increasing pSTAT3 expression. The contacting may be performed in vitro. The contacting may be performed in vivo. Methods for assaying an increase or decrease in pSTAT3 expression are well known in the art.

In another aspect, there is provided a method of modulating the activity of a Gp130 receptor in a cell. The method includes contacting a cell which includes a Gp130 receptor with a compound as disclosed herein. In embodiments, the activity of the Gp130 receptor is increased. In embodiments, the activity of the Gp130 receptor is decreased or inhibited.

In another aspect, there is provided a method of agonizing Gp130 in a cell. The method includes contacting a cell which includes a Gp130 receptor with a compound as disclosed herein.

In another aspect, there is provided a method of inhibiting the release of lactate dehydrogenase (LDH) from a cell, the method comprising contacting the cell with a compound according to the present disclosure.

In another aspect, there is provided a method of suppressing over-activation of a N-methyl-D-aspartate (NMDA) receptor the method comprising contacting a cell with a compound according to the present disclosure.

In another aspect, there is provided a method of protecting a cell from amyloid-beta-related toxicity, the method comprising contacting the cell with a compound according to the present disclosure.

Compounds

In an aspect, provided herein are compounds useful for treating a neurological condition in a subject in need thereof, comprising compounds in accordance with the present disclosure (e.g. the compounds of Formulae I, II and/or III including all embodiments thereof).

In another aspect, a compound having the structure of Formula (II) is provided:

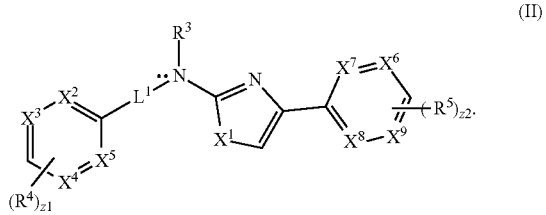

(II)

$R^4$ and $R^5$ are as described above, including embodiments thereof. For example, in embodiments, $R^4$ and $R^5$ may independently be halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $X^1$ is as described above. For example, $X^1$ may be S, Se or O. $X^2$, $X^3$, $X^4$, $X^5$, $X^6$, $X_7$, $X^8$ and $X^9$ are as described above, including embodiments thereof. For example, $X^2$, $X^3$, $X^4$, $X^5$, $X^6$, $X^7$, $X^8$ and $X^9$ may independently be CH or N. The integers z1 and z2 are as described above, including embodiments thereof. For example, z1 and z2 may independently be an integer from 0 to 5. $L^1$ is unsubstituted $C_1$-$C_{10}$ alkyl.

In another aspect, a compound having the structure of Formula (III) is provided:

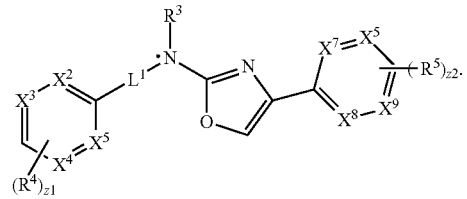

(III)

$R^4$ and $R^5$ are independently halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl. $X^1$ is as described above. For example, $X^1$ may be S, Se or O. $X^2$, $X^3$, $X^4$, $X^5$, $X^6$, $X^7$, $X^8$ and $X^9$ are as described above, including embodiments thereof. For example, $X^2$, $X^3$, $X^4$, $X^5$, $X^6$, $X^7$, $X^8$ and $X^9$ may independently be CH or N. The integers z1 and z2 are as described above, including embodiments thereof. For example, z1 and z2 may independently be an integer from 0 to 5. $L^1$ is unsubstituted $C_1$-$C_{10}$ alkyl.

In embodiments, $L^1$ is a bond. In embodiments, $L^1$ is unsubstituted $C_1$-$C_{10}$ alkyl.

In embodiments, $R^4$ of Formulae II and Formula III is substituted alkyl substituted with a substituent group, a size-limited substituent group, or lower substituent group. In embodiments, $R^4$ is substituted cycloalkyl substituted with a substituent group, a size-limited substituent group, or lower substituent group. In embodiments, $R^4$ is substituted heteroalkyl substituted with a substituent group, a size-limited substituent group, or lower substituent group. In embodiments, $R^4$ is substituted heterocycloalkyl substituted with a substituent group, a size-limited substituent group, or lower substituent group. In embodiments, $R^4$ is substituted aryl substituted with a substituent group, a size-limited substituent group, or lower substituent group. In embodiments, $R^4$ is substituted heteroaryl substituted with a substituent group, a size-limited substituent group, or lower substituent group. In embodiments, $R^4$ is $R^{400}$-substituted or unsubstituted alkyl, $R^{400}$-substituted or unsubstituted heteroalkyl, $R^{400}$-substituted or unsubstituted cycloalkyl, $R^{400}$-substituted or unsubstituted heterocycloalkyl, $R^{400}$-substituted or unsubstituted aryl or $R^{400}$-substituted or unsubstituted heteroaryl. In embodiments, $R^{400}$ is independently halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —$OCF_3$, —$OCCl_3$, —$OCBr_3$, —$OCI_3$, —$OCHF_2$, —$OCHCl_2$, —$OCHBr_2$, —$OCHI_2$, $R^{400}$-substituted or unsubstituted alkyl, $R^{400}$-substituted or unsubstituted heteroalkyl, $R^{400}$-substituted or unsubstituted cycloalkyl, $R^{400}$ substituted or unsubstituted heterocycloalkyl, $R^{400}$-substituted or unsubstituted aryl or $R^{400}$-substituted or unsubstituted heteroaryl. In embodiments, $R^{400}$ is halogen, —$CF_3$, —$CCl_3$, —$CBr_3$, —$CI_3$, —CN, —OH, $NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl or unsubstituted heteroaryl. In embodiments, R$^4$ is unsubstituted alkyl, unsubstituted cycloalkyl, unsubstituted heteroalkyl, unsubstituted heterocycloalkyl, unsubstituted aryl, or unsubstituted heteroaryl.

In embodiments, R$^5$ of Formulae II and Formula III is substituted alkyl substituted with a substituent group, a size-limited substituent group, or lower substituent group. In embodiments, R$^5$ is substituted cycloalkyl substituted with a substituent group, a size-limited substituent group, or lower substituent group. In embodiments R$^5$ is substituted heteroalkyl substituted with a substituent group, a size-limited substituent group, or lower substituent group. In embodiments, R$^5$ is substituted heterocycloalkyl substituted with a substituent group, a size-limited substituent group, or lower substituent group. In embodiments, R$^5$ is substituted aryl substituted with a substituent group, a size-limited substituent group, or lower substituent group. In embodiments, R$^5$ is substituted heteroaryl substituted with a substituent group, a size-limited substituent group, or lower substituent group. In embodiments, R$^5$ is R$^{500}$ substituted or unsubstituted alkyl, R$^{500}$-substituted or unsubstituted heteroalkyl, R$^{500}$-substituted or unsubstituted cycloalkyl, R$^{500}$-substituted or unsubstituted heterocycloalkyl, R$^{500}$-substituted or unsubstituted aryl or R$^{500}$-substituted or unsubstituted heteroaryl. In embodiments, R$^5$ is halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, R$^{500}$-substituted or unsubstituted alkyl, R$^{500}$-substituted or unsubstituted heteroalkyl, R$^{500}$-substituted or unsubstituted cycloalkyl, R$^{500}$-substituted or unsubstituted heterocycloalkyl, R$^{500}$-substituted or unsubstituted aryl or R$^{500}$-substituted or unsubstituted heteroaryl. In embodiments, R$^{500}$ is independently halogen, —CF$_3$, —CCl$_3$, —CBr$_3$, —CI$_3$, —CN, —OH, NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)—OH, —NHOH, —OCF$_3$, —OCCl$_3$, —OCBr$_3$, —OCI$_3$, —OCHF$_2$, —OCHCl$_2$, —OCHBr$_2$, —OCHI$_2$, unsubstituted alkyl, unsubstituted heteroalkyl, unsubstituted cycloalkyl, unsubstituted heterocycloalkyl, unsubstituted aryl or unsubstituted heteroaryl. In embodiments, R$^5$ is unsubstituted alkyl, unsubstituted cycloalkyl, unsubstituted heteroalkyl, unsubstituted heterocycloalkyl, unsubstituted aryl, or unsubstituted heteroaryl.

Pharmaceutical Compositions

In another aspect, provided are pharmaceutical compositions and formulations for treating a neurological condition in a subject in need thereof, comprising compounds in accordance with the present disclosure (e.g. the compounds of Formulae I, II and/or III including all embodiments thereof).

In embodiments, there is provided a pharmaceutical composition comprising a compound in accordance with the present disclosure and one or more pharmaceutically acceptable excipients. In embodiments, the pharmaceutical compositions, the compound, or pharmaceutically acceptable salt thereof, is included in a therapeutically effective amount.

The pharmaceutical composition may be prepared and administered in a wide variety of dosage formulations. Compounds described may be administered orally, rectally, or by injection (e.g. intravenously, intramuscularly, intracutaneously, subcutaneously, intraduodenally, or intraperitoneally).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present disclosure may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present disclosure can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present disclosure into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' disclosure. Adjustment and manipulation of established dosages (e.g., frequency and duration) are well within the ability of those skilled in the art.

The compounds described herein can be used in combination with one another, with other active compounds or drugs known to be useful in treating neurological conditions (e.g. Alzheimer's Disease), or with adjunctive agents that may not be effective alone, but may contribute to the efficacy of the active agent.

In an embodiment, the neurological condition is a neurological disorder or a neurodegenerative disease selected from the group consisting of Alzheimer's Disease, Amyotrophic Lateral Sclerosis, Friedreich's Ataxia, Huntington's Disease, Lewy Body Disease, Parkinson's Disease, Spinal Muscular Atrophy, Alpers' Disease, Batten Disease, Cerbro-Oculo-Facio Skeletal Syndrome, Corticobasal Degeneration, Gerstmann-Straussler-Scheinker Disease, Kuru, Leigh's Disease, Monomelic Amyotrophy, Multiple System Atrophy, Shy-Drager Syndrome, Neurodegeneration with Brain Iron Accumulation, Opsoclonus Myoclonus, Prion Disease, Progressive Multifocal Leukoencephalpathy and Striatonigral Degeneration, traumatic brain injury (TBI), stroke, intracellular hemorrhage and ischemia and reperfusion injury, epilepsy, seizures associated with epilepsy, seizures associated with neurological conditions, and cerebrovascular dementia through inhibition of Abeta-mediated cell death of human cerebrovascular smooth muscle cells.

In embodiments, the composition further comprises one or more other active compounds or drugs known to be useful in treating a neurological condition. In embodiments, the compounds described herein may be co-administered with one another or with one or more other active compounds or drugs known to be useful in treating a neurological condition.

Other active compounds or drugs useful for treating neurological conditions include, but are not intended to be limited to, acetylcholinesterase inhibitors such as, for example, Donezepil (Aricept), Rivastigmine (EXELON), Galantamine (RAZADINE), tacrine (COGNEX); the NMDA antagonist known as Memantine (NAMENDA) or in combination with Aricept and Namenda (Namzaric), tropisetron, Solanezumab, Bapineuzmab, Alzemed, Flurizan, ELND005, Valproate, Semagacestat, Rosiglitazone, Phenserine, Cernezumab, Dimebon, EGCg, Gammagard, PBT2, PF04360365, NIC5-15, Bryostatin-1, AL-108, Nicotinamide, EHT-0202, BMS708163, NP 12, Lithium, ACC001, AN1792, ABT089, NGF, CAD106, AZD3480, SB742457, AD02, Huperzine-A, EVP6124, PRX03140, PUFA, HF02, MEM3454, TTP448, PF-04447943, Ent., GSK933776, MABT5102A, Talsaclidine, UB311, Begacestat, $R^{1450}$, PF3084014, V950, E2609, MK0752, CTS21166, AZD-3839, AZD-3293, LY2886721, LY2811376, CHF5074, verubecestat (MK-8931), NB-360, CNP520, JNJ-54861911, R 05508887, anti-inflammatories (e.g., Flurizan (Myriad Genetics), Dapsone, anti-TNF antibodies (e.g., etanercept (Amgen/Pfizer)), and the like, statins (e.g., atorvastatin (LIPITOR®), simvastatin (ZOCOR®, etc.), BACE inhibitors and the like.

For preparing pharmaceutical compositions from compounds described herein, pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutical composition may be intended for intravenous use. The pharmaceutically acceptable excipient can include buffers to adjust the pH to a desirable range for intravenous use. Many buffers including salts of inorganic acids such as phosphate, borate, and sulfate are known.

The pharmaceutical composition may include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

Therapeutically effective amounts for use in humans may be determined from animal models. For example, a dose for humans can be formulated to achieve a concentration that has been found to be effective in animals. The dosage in humans can be adjusted by monitoring response of the constipation or dry eye to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

EMBODIMENTS

Embodiment 1

A method for treating a neurological condition in a subject in need thereof, the method comprising administering to the subject a compound having a structure of Formula (I):

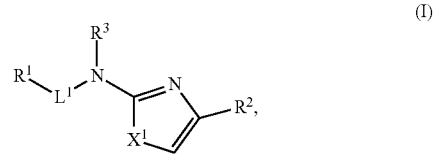

or
a pharmaceutically acceptable salt thereof,
wherein
$X^1$ is S, Se or O;
$L^1$ is $C_1$-$C_{10}$ unsubstituted alkyl or a bond;

R¹ is hydrogen, halogen, —CF₃, —CCl₃, —CBr₃, —CI₃, —CN, —OH, NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and R² and R³ are independently hydrogen, halogen, —CF₃, —CCl₃, —CBr₃, —CI₃, —CN, —OH, NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Embodiment 2

The method of Embodiment 1, wherein X¹ is S.

Embodiment 3

The method of Embodiment 1, wherein X¹ is O.

Embodiment 4

The method of Embodiment 1, wherein X¹ is Se.

Embodiment 5

The method of Embodiment 1, wherein L¹ is unsubstituted C₁-C₁₀ alkyl.

Embodiment 6

The method of Embodiment 1, wherein L¹ is a bond.

Embodiment 7

The method of any one of Embodiments 1 to 6, wherein R³ is hydrogen, methyl or substituted or unsubstituted cyclopropyl.

Embodiment 8

The method of any one of Embodiments 1 to 6, wherein R³ is hydrogen.

Embodiment 9

The method of any one of Embodiments 1 to 8, wherein R¹ is substituted or unsubstituted aryl or substituted or unsubstituted heteroaryl.

Embodiment 10

The method of any one of Embodiments 1 to 8, wherein R¹ is substituted or unsubstituted heteroaryl.

Embodiment 11

The method of any one of Embodiments 1 to 8, wherein R¹ is substituted or unsubstituted pyridinyl or substituted or unsubstituted pyrimidinyl.

Embodiment 12

The method of any one of Embodiments 1 to 8, wherein R¹ is substituted or unsubstituted aryl.

Embodiment 13

The method of any one of Embodiments 1 to 8, wherein R¹ is substituted or unsubstituted phenyl.

Embodiment 14

The method of any one of Embodiments 1 to 13, wherein R² is substituted or unsubstituted aryl or substituted or unsubstituted heteroaryl.

Embodiment 15

The method of any one of Embodiments 1 to 13, wherein R² is substituted or unsubstituted aryl.

Embodiment 16

The method of any one of Embodiments 1 to 13, wherein R² is substituted or unsubstituted phenyl.

Embodiment 17

The method of any one of Embodiments 1 to 13, wherein R² is substituted or unsubstituted heteroaryl.

Embodiment 18

The method of any one of Embodiments 1 to 13, wherein R² is substituted or unsubstituted pyridinyl or substituted or unsubstituted pyrimidinyl.

Embodiment 19

The method of any one of Embodiments 1 to 18 wherein the compound has the structure of Formula (II):

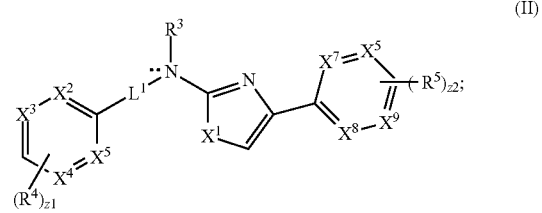

wherein

R⁴ and R⁵ are independently halogen, —CF₃, —CCl₃, —CBr₃, —CI₃, —CN, —OH, NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;

$X^2$, $X^3$, $X^4$, $X^5$, $X^6$, $X^7$, $X^8$ and $X^9$ are independently CH or N; and z1 and z2 are independently an integer from 0 to 5.

Embodiment 20

The method of Embodiment 19 having the structure of Formula (IIA):

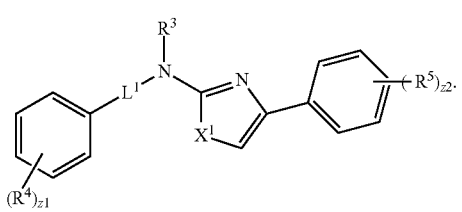

(IIA)

Embodiment 21

The method of Embodiment 19 wherein the compound has the structure of Formula (IB):

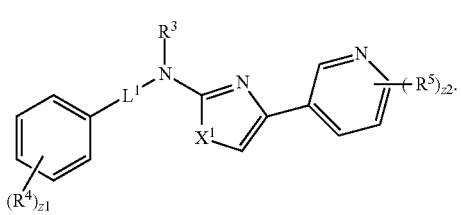

(IIB)

Embodiment 22

The method of Embodiment 19 wherein the compound has the structure of Formula (IIC):

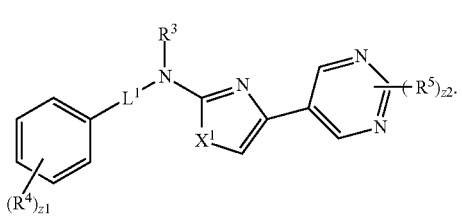

(IIC)

Embodiment 23

The method of any one of Embodiments 1 to 22, wherein $R^4$ and $R^5$ are independently halogen, methyl, and —CF$_3$ Embodiment 24

The method of any one of Embodiments 1 to 22, wherein if $R^4$ or $R^5$ are a methyl, the methyl is a deuterated methyl.

Embodiment 25

The method of any one of Embodiments 1 to 24, wherein z1 and z2 are independently 0 or 1.

Embodiment 26

The method of Embodiment 1, wherein the compound is selected from the group consisting of:

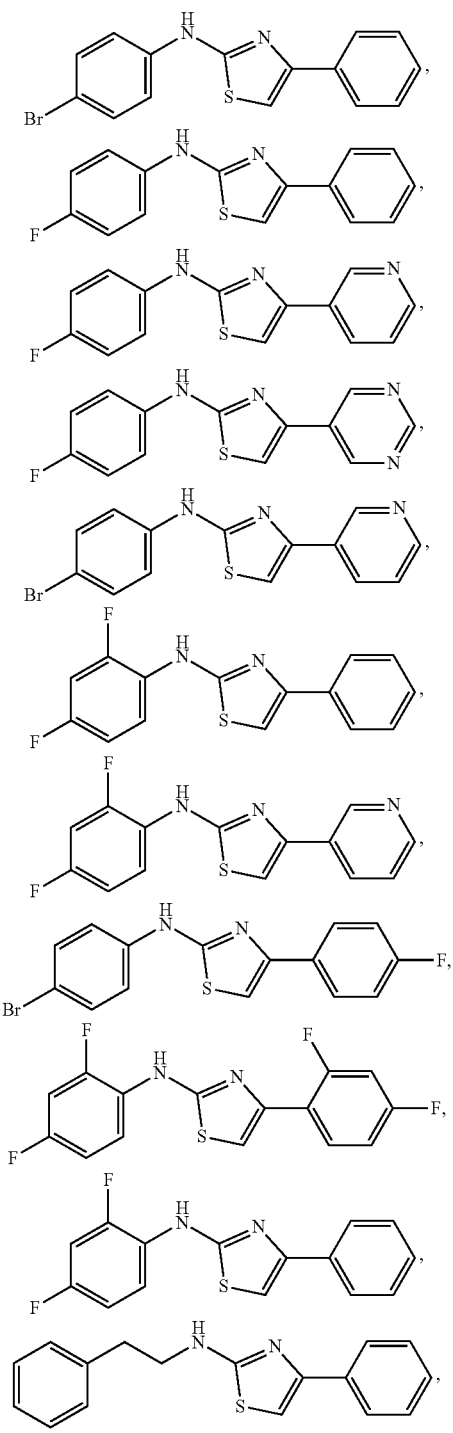

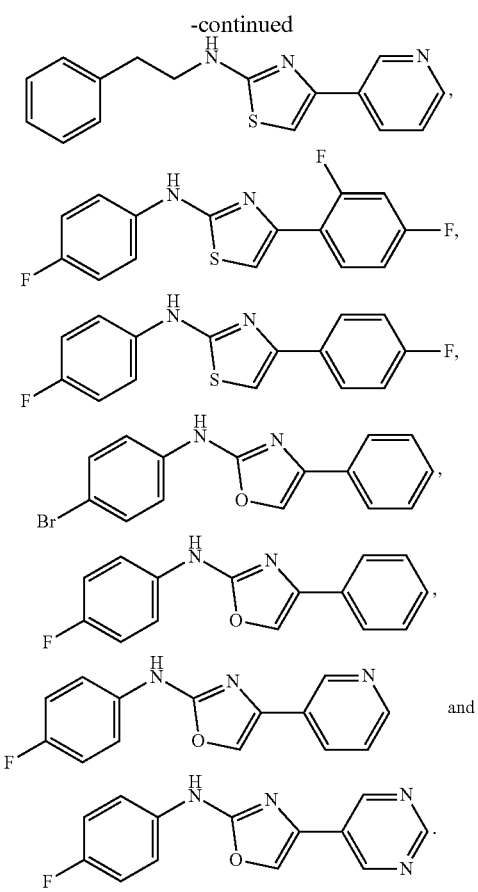

Embodiment 27

The method of any one of Embodiments 1-26, wherein the neurological condition is a neurological disorder or neurodegenerative disease selected from the group consisting of Alzheimer's Disease, Amyotrophic Lateral Sclerosis, Friedreich's Ataxia, Huntington's Disease, Lewy Body Disease, Parkinson's Disease, Spinal Muscular Atrophy, Alpers' Disease, Batten Disease, Cerbro-Oculo-Facio Skeletal Syndrome, Corticobasal Degeneration, Gerstmann-Straussler-Scheinker Disease, Kuru, Leigh's Disease, Monomelic Amyotrophy, Multiple System Atrophy, Shy-Drager Syndrome, Neurodegeneration with Brain Iron Accumulation, Opsoclonus Myoclonus, Prion Disease, Progressive Multifocal Leukoencephalpathy and Striatonigral Degeneration, traumatic brain injury (TBI), stroke, intracellular hemorrhage and ischemia and reperfusion injury, epilepsy, seizures associated with epilepsy, seizures associated with neurological conditions, and cerebrovascular dementia through inhibition of Abeta-mediated cell death of human cerebrovascular smooth muscle cells.

Embodiment 28

The method of any one of Embodiments 1-27, wherein the neurological condition is a neurological disorder.

Embodiment 29

The method of any one of Embodiments 1-27, wherein the neurological condition is a neurodegenerative disease.

Embodiment 30

The method of any one of Embodiments 1-27, wherein the neurological condition is Alzheimer's Disease.

Embodiment 31

The method of any one of Embodiments 1-30, wherein the administering comprises contacting the compound with a cell of the subject, wherein the cell comprises a Gp130 receptor, and wherein the compound is capable of binding to the Gp130 receptor.

Embodiment 32

The method of Embodiment 31, wherein the compound is capable of binding to binding domain 4 and binding domain 5 of the Gp130 receptor.

Embodiment 33

The method of Embodiment 31, wherein the compound is capable of binding to binding domain 4 of the Gp130 receptor.

Embodiment 34

The method of Embodiment 31, wherein the compound is capable of binding to binding domain 5 of the Gp130 receptor.

Embodiment 35

The method of any one of Embodiments 1-34, wherein the cell is a human cell.

Embodiment 36

The method of Embodiment 35 wherein the cell is a neuron.

Embodiment 37

The method of any one of Embodiments 1 to 36, further comprising co-administering a compound for treating a neurological condition.

Embodiment 38

A compound having the structure of Formula (II):

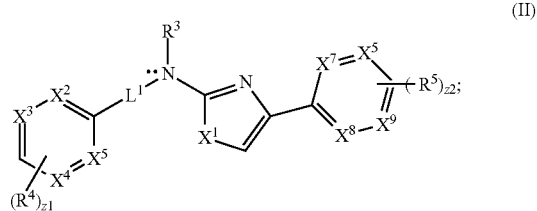

wherein
$R^4$ and $R^5$ are independently halogen, $-CF_3$, $-CCl_3$, $-CBr_3$, $-CI_3$, $-CN$, $-OH$, $NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC$ (O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;

$X^2$, $X^3$, $X^4$, $X^5$, $X^6$, $X^7$, $X^8$ and $X^9$ are independently CH or N;

z1 and z2 are independently an integer from 0 to 5; and $L^1$ is unsubstituted $C_1$-$C_{10}$ alkyl.

Embodiment 39

A compound having the structure of Formula (III):

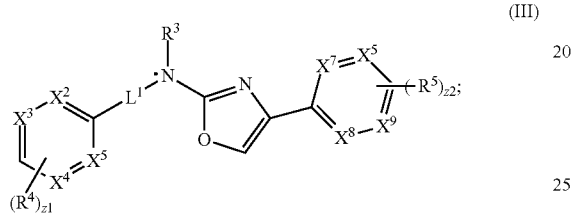

wherein $R^4$ and $R^5$ are independently halogen, —CF₃, —CCl₃, —CBr₃, —CI₃, —CN, —OH, NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)—OH, —NHOH, —OCF₃, —OCCl₃, —OCBr₃, —OCI₃, —OCHF₂, —OCHCl₂, —OCHBr₂, —OCHI₂, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;

$X^2$, $X^3$, $X^4$, $X^5$, $X^6$, $X^7$, $X^8$ and $X^9$ are independently CH or N;

z1 and z2 are independently an integer from 0 to 5; and $L^1$ is a bond or unsubstituted $C_1$-$C_{10}$ alkyl.

Embodiment 40

The compound of Embodiment 39 wherein $L^1$ is a bond.

Embodiment 41

The compound of Embodiment 39 wherein $L^1$ is unsubstituted $C_1$-$C_{10}$ alkyl.

Embodiment 42

A compound selected from the group consisting of:

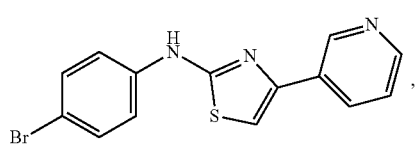

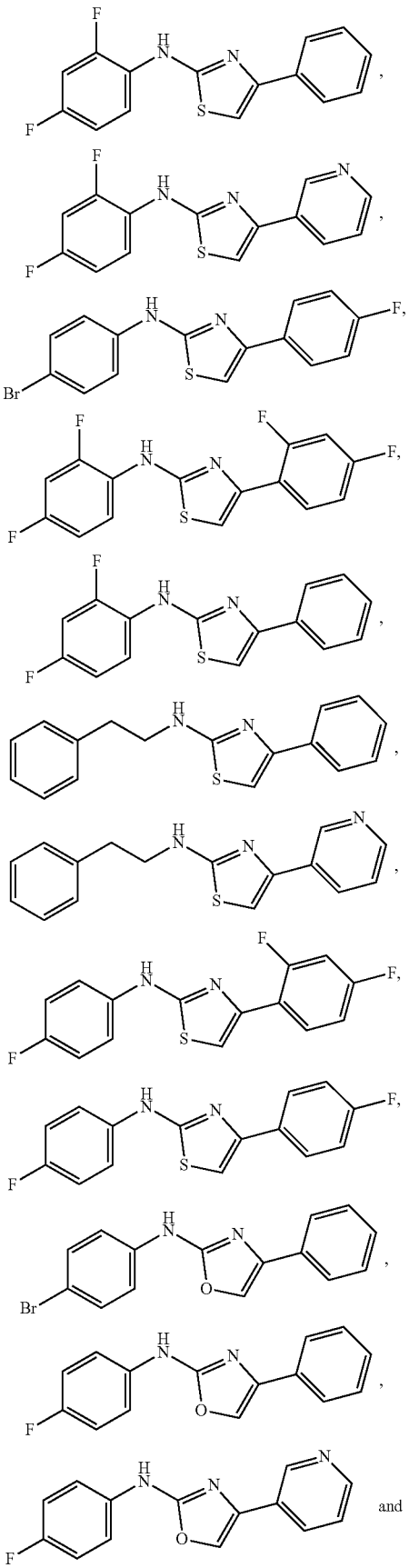

and

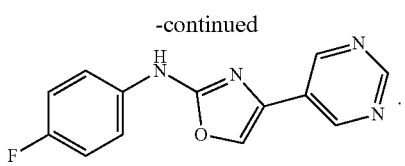

Embodiment 43

A pharmaceutical composition comprising the compound of any one of Embodiments 38 to 42 and a pharmaceutically acceptable excipient.

Embodiment 44

The pharmaceutical composition of Embodiment 43, further comprising a compound for treating a neurological condition.

Embodiment 45

The pharmaceutical composition of Embodiment 44, wherein the neurological condition is a neurological disorder or neurodegenerative disease selected from the group consisting of Alzheimer's Disease, Amyotrophic Lateral Sclerosis, Friedreich's Ataxia, Huntington's Disease, Lewy Body Disease, Parkinson's Disease, Spinal Muscular Atrophy, Alpers' Disease, Batten Disease, Cerbro-Oculo-Facio Skeletal Syndrome, Corticobasal Degeneration, Gerstmann-Straussler-Scheinker Disease, Kuru, Leigh's Disease, Monomelic Amyotrophy, Multiple System Atrophy, Shy-Drager Syndrome, Neurodegeneration with Brain Iron Accumulation, Opsoclonus Myoclonus, Prion Disease, Progressive Multifocal Leukoencephalpathy and Striatonigral Degeneration, traumatic brain injury (TBI), stroke, intracellular hemorrhage and ischemia and reperfusion injury, epilepsy, seizures associated with epilepsy, seizures associated with neurological conditions, and cerebrovascular dementia through inhibition of Abeta-mediated cell death of human cerebrovascular smooth muscle cells.

Embodiment 46

The pharmaceutical composition of Embodiment 45, wherein the neurological condition is a neurological disorder.

Embodiment 47

The pharmaceutical composition of Embodiment 45, wherein the neurological condition is a neurodegenerative disease.

Embodiment 48

The pharmaceutical composition of Embodiment 45, wherein the neurological condition is Alzheimer's Disease.

Other Embodiments

There are provided, inter alia, compounds and method useful for the treatment of Alzheimer's Disease. Humanin (HN), a 24-amino acid bioactive peptide, has been shown to increase cell survival of neurons after exposure to Aβ and NMDA-induced toxicity and thus could be beneficial in the treatment of Alzheimer's disease (AD). The protection by HN is primarily through binding to the Gp130 receptor, which is part of a trimeric cell surface complex involving CNTF/WSX1/GP130. We report here for the first time the elucidation of the binding site of HN to Gp130 through modeling, and the identification of a small molecule mimetic that binds at the HN binding site on the receptor. This small molecule mimetic lead candidate, N-(4-fluorophenyl)-4-phenylthiazol-2-amine (compound 2), was identified through screening and exploratory medicinal chemistry using a microfluidic flow chemistry approach to facilitate the syntheses of new analogs of an original 'hit' and SAR optimization. This is a green-chemistry approach for synthesis of bioactive small molecules. The analogs generated have enabled us to gain chemical insights into the SAR of Gp130 agonists to protect primary neurons against NMDA-induced excitotoxicity. HN due to its peptidic nature presents challenges in development as a therapeutic for AD. In contrast, the HN mimetic lead candidate 2 was shown to have good oral brain permeability and is a good candidate for further evaluation of the neuroprotection through the Gp130 receptor agonism mechanism in NMDA-induced neurotoxicity animal models.

Embodiment P1

A compound having structure of Formula (I):

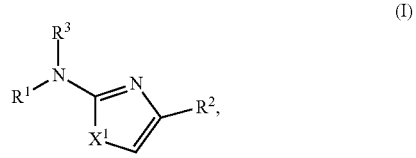

or pharmaceutically acceptable salt, ester, amide, solvate, hydrate, or prodrug thereof;

wherein $X^1$ is a heteroatom;

$R^1$ is hydrogen, halogen, —$CF_3$, —$CCl_3$, —$CBr_3$, —$CI_3$, —CN, —OH, —SH, —$NH_2$, —C(O)$NH_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl; and $R^2$ and $R^3$ are independently hydrogen, halogen, —$CF_3$, —$CCl_3$, —$CBr_3$, —$CI_3$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

Embodiment P2

The compound according to Embodiment P1, wherein $X^1$ is S.

Embodiment P3

The compound according to Embodiment P1, wherein $X^1$ is O.

Embodiment P4

The compound according to Embodiment P1, wherein $X^1$ is Se.

Embodiment P5

The compound of any one of Embodiments P1 to P4, wherein $R^3$ is hydrogen, methyl or substituted or unsubstituted cyclopropyl.

Embodiment P6

The compound of any one of Embodiments P1 to P5, wherein $R^3$ is hydrogen.

Embodiment P7

The compound of any one of Embodiments P1 to P6, wherein $R^1$ is substituted or unsubstituted aryl or substituted or unsubstituted heteroaryl.

Embodiment P8

The compound of any one of Embodiments P1 to P6, wherein $R^1$ is substituted or unsubstituted heteroaryl.

Embodiment P9

The compound of any one of Embodiments P1 to P6, wherein $R^1$ is substituted or unsubstituted pyridinyl or substituted or unsubstituted pyrimidinyl.

Embodiment P10

The compound of any one of Embodiments P1 to P6, wherein $R^1$ is substituted or unsubstituted aryl.

Embodiment P11

The compound of any one of Embodiments P1 to P6, wherein $R^1$ is substituted or unsubstituted phenyl.

Embodiment P12

The compound of any one of Embodiments P1 to P11, wherein $R^2$ is substituted or unsubstituted aryl or substituted or unsubstituted heteroaryl.

Embodiment P13

The compound of any one of of Embodiments P1 to P11, wherein $R^2$ is substituted or unsubstituted aryl.

Embodiment P14

The compound of any one of of Embodiments P1 to P11, wherein $R^2$ is substituted or unsubstituted phenyl.

Embodiment P15

The compound of any one of of Embodiments P1 to P11 wherein $R^2$ is substituted or unsubstituted heteroaryl

Embodiment P16

The compound of any one of of Embodiments P1 to P11, wherein $R^2$ is substituted or unsubstituted pyridinyl or substituted or unsubstituted pyrimidinyl.

Embodiment P17

The compound according to any one of Embodiments P1 to P16, having the structure of Formula (II):

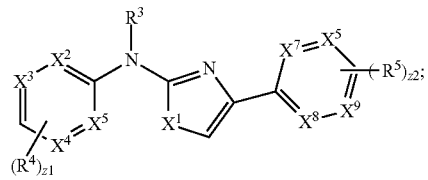

wherein
$R^4$ and $R^5$ are independently halogen, —$CF_3$, —$CCl_3$, —$CBr_3$, —$CI_3$, —CN, —OH, —SH, —$NH_2$, —C(O)$NH_2$, substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl;
$X^2, X^3, X^4, X^5, X^6, X^7, X^8$ and $X^9$ are independently C or N; and
z1 and z2 are independently an integer from 0 to 5.

Embodiment P18

The compound according to Embodiment P17, having structure of Formula (IIA):

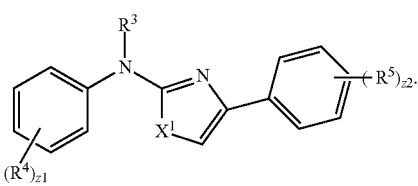

Embodiment P19

The compound according to Embodiment P17, having structure of Formula (IIB):

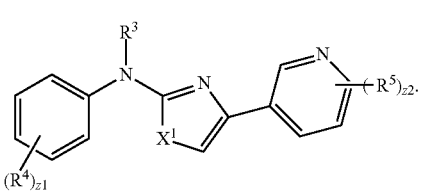

Embodiment P20

The compound according to Embodiment P17, having structure of Formula (IIC):

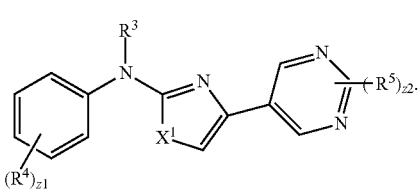

Embodiment P21

The compound of any one of of Embodiments P1-P20, wherein $R^4$ and $R^5$ are independently halogen, methyl, and —$CF_3$.

Embodiment P22

The compound of any one of of Embodiments P1-P20, wherein if $R^4$ or $R^5$ are a methyl, the methyl is a deuterated methyl.

Embodiment P23

The compound of any one of of Embodiments P1-P22, wherein z1 and z2 are independently 0 or 1.

Embodiment P24

A method of increasing pSTAT3 expression in a cell, the method comprising contacting a cell comprising a Gp130 receptor with a binding site Gp130 receptor agonist according to any one of Embodiments P1-P23.

Embodiment P25

A method of modulating the activity of a Gp130 receptor in a cell, the method comprising contacting a cell comprising a Gp130 receptor with a binding site Gp130 receptor agonist according to any one of Embodiments P1-P23.

Embodiment P26

A method of agonizing Gp130 in a cell, the method comprising contacting a cell comprising a Gp130 receptor with a binding site Gp130 receptor agonist according to any one of Embodiments P1-P23.

Embodiment P27

A method for treatment of Alzheimer's disease, the method comprising administering to a subject in need an effective amount of a compound according to any one of Embodiments P1-P23.

EXAMPLES

The following examples are provided for the purpose of illustrating certain embodiments of the methods and compositions disclosed herein and should not be interpreted as limiting the scope of the invention.

Introduction to Examples

In 2001, Hashimoto et al. [PNAS 2001, USA 98:6336] identified humanin (HN) as a 24-amino acid peptide which protected cells from amyloid-beta (Aβ)-related toxicity. It was subsequently disclosed that HN confers this protection through agonism of Gp130 binding receptor by a showing that antibody neutralization of Gp130 eradicated HN protection of F11 cells from V642I-APP-induced death, and that tyrosine phosphorylation of STAT3 (pTyr[705]-STAT3) was increased in the presence of HN [Hashimoto et al. 2009, Mol Biol Cell 20:2864].

Muzumder and coworkers reported a decrease in the endogenous HN plasma level with age, suggesting that decreased HN levels may be linked to cognitive decline during aging [Muzumder et al. 2009, PLoS One. 4 (7), e6334]. The potent HN analog HNG, HN with a substitution of serine 14 to glycine, showed neuroprotection against Aβ1-42-induced death in primary neurons at nanomolar levels in vitro [Hashimoto et al. 2001, PNAS 98 (11), 6336]. HN exerts its function through binding to both extracellular receptors and intracellular binding partners [Gong et al. 2014, Front. Endocrinol. (Lausanne), 5, 210]. The proposed extracellular binding partners include G-protein coupled receptors, formyl peptide receptor like (FPRL)-1 and 2 [Harada et al. 2004, Biochem. Biophys. Res. Commun., 324 (1), 255] [Ying et al. 2004, J. Immunol., 172 (11), 7078]; and a trimeric receptor complex of Gp130, ciliary neurotrophic factor receptor c (CNTFR), and the IL-27 receptor subunit, WSX-1[Hashimoto et al. 2009, Mol Biol Cell 20:2864].

Hashimoto and coworkers reported that HN confers its protection against Aβ1-42 neurotoxicity through agonism of Gp130 and that this is required for HN-mediated protection against Aβ1-42-induced death. In F11 neurohybrid cells transfected with amyloid precursor protein (APP) with the familial AD mutant V642I-APP, there is significant neuronal cell death in vitro. Treatment with HN protects against this cell death, but this protection is eradicated if the F11 cells are also treated with a Gp130 neutralizing antibody. In addition, the study shows that activation of STAT3 is essential for the HN activity, thus treatment of the F11 cells with HN resulted in up-regulation of the tyrosine phosphorylation of STAT3 (pTyr705-STAT3) [Hashimoto et al. 2009, Mol Biol Cell 20:2864]. These results support the previous reports that suggest that an increase in Gp130 signaling may be of benefit in AD [Matsuoka et al. 2010 *Mol Neurobiol.* 41:22]. Others have suggested that the anti-AD therapeutic benefits of HN could be through interaction with residues (17-28) of monomeric A13 that results in prevention of Aβ oligomerization and provides neuroprotection [Maftei et al. 2012, 18:373].

Since an increase in Gp130 signaling may be of benefit in AD [Matsuoka et al. 2010 *Mol Neurobiol.* 41:22], HN has been under study as a possible therapeutic for AD. Recent studies [Cui 2014 *Scientific World Journal* 341529] have additionally shown that HN, similar to known NMDA receptor antagonist MK-801, rescues neurons from NMDA-mediated toxicity. Excitotoxicity through NMDA receptor over-activation is associated with disease progression in AD [Sonkusare 2005, *Pharmacol Res* 51(1): 1]. Therefore over the years there have been significant drug discovery efforts to identify new NMDA receptor antagonists for treatment of AD and other neurological disorders such as Parkinson's disease, cerebral ischemia, and stroke wherein excitotoxicity is thought to play a role. However, such antagonists have been associated with significant adverse effects and neurotoxicity. A partial antagonist of the NMDA receptor called memantine (Namenda) was approved for AD as a symptomatic therapy over a decade ago, but provides only limited benefit [Matsunaga et al. 2015, *PLoS One,* 10(4):e0123289]. Accordingly, without wishing to be bound any theory, it is believed that mimetics of HN are useful for treatment of AD.

HN, however, has the disadvantage of low brain permeability being a peptide, which present challenges in its development as a therapeutic. Although some efficacy of HN derivative HNG has been seen in murine models of AD after intranasal delivery [Niikura 2011 PLoS One 6(1):e16259] and intraperitoneal injection [Zhang Pharmacol Biochem Behav 2012 100(3):361], these delivery methods are not readily adaptable to human patients. Therefore, it is believed that a small molecule Gp130 agonist mimetic of HN would allow for more rapid development and ease of delivery. Such compounds could be neuroprotective and could describe a new pharmacological class of AD therapeutic agents. An efficacious compound from this class may be used alone or in combination with other anti-AD drugs.

Without wishing to be bound by any theory, in an embodiment, compound PA1, and analogs thereof, may function as a Leukemia Inhibitory Factor (LIF) signaling cascade agonist. Indeed, computer modeling studies indicate that such compounds interact with Gp130. Both LIF and interleukin-6 (IL-6) have receptors that, upon ligand binding, interact with 'signal transducer' Gp130, which initiates a signaling cascade comprising activation of the JAK-STAT pathway, phosphorylation of STAT3 (pSTAT3), and ultimately regulation of gene expression. See e.g., Hurt & Farrar, *Blood* 110:1086. PA1 has been shown to increase pSTAT3 and reduce apoptosis of human chondrocytes.

Figure 3:
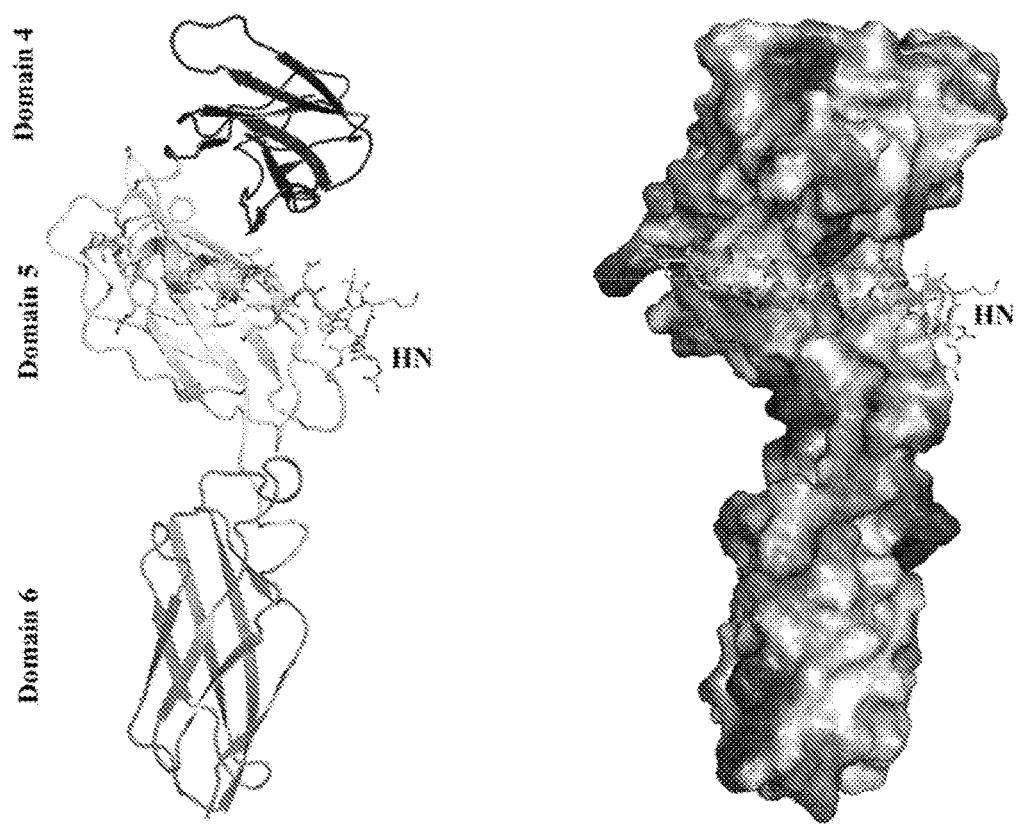
FIG. 3. Binding site of humanin (HN) in the extracellular domains (D4-D6) of gp130. Left, the structure of the indicated gp130 domains bound to HN is shown in ribbon diagram representation. Right, molecular surface representation of the gp130 extracellular domains D4-D6 shown with HN (gray) bound at the interface between D4 and D5 domains. The residues in HN are shown in stick representation.

In embodiments, HN acts to rescue the NMDA-mediated toxicity in neurons through its interaction with the domain-4 and 5 (D4 D5) of the Gp130 receptor (FIG. 1D; FIG. 3). Provided herein, inter alia, is computational modeling of HN peptide and Gp130. Also provided are screening and exploratory medicinal chemistry approaches identifying small molecule Gp130 agonists that also rescues neurons from NMDA-mediated toxicity. We also found that the presence of a Gp130 antagonist, SC144 [Xu et al. 2013, N. Mol. Cancer Ther. 12:937], reverses the neuroprotection conferred by certain agonists. Interestingly, our modeling analysis shows that, in embodiments, both asmall molecule Gp130 agonist and an antagonist bind to the same Gp130 receptor domain-4 as HN. Thus, in embodiments, small molecule Gp130 agonists may be HN mimetics. In embodiments, small molecule Gp130 agonists suppress the NMDA receptor over-activation and excitotoxicity and provide a new therapeutic development in neurodegenerative disorders such as AD.

Certain examples provided herein begin with a screening hit compound which was found to be a regulator of cartilage growth and differentiation (RCGD)-423 (compound 1(PA1)) and was identified through an HTS effort using a 200,000-compound chemical library to find compounds that increase articular chondrocyte activation and facilitate joint repair. A compound 1 (PA1) was shown to be a Gp130 agonist that initiates a signaling cascade comprising activation of the JAK-STAT3 pathway, phosphorylation of STAT3 (pSTAT3), and ultimately regulation of gene expression (Shkhyan et al. submitted manuscript).

In certain examples provided herein, a library of analogs have been discovered that are Gp130 agonists. Also provided is methods for providing seamless integration of state-of-the-art flow-chemistry for a structure-activity relationship (SAR) campaign with chemical biology. Continuous flow chemistry enables a rapid gain in chemical insights into SAR needed for Gp130 agonism and neuroprotection and thus facilitates syntheses of new analogs using a green chemistry approach. In embodiments, this approach provides a cleaner reaction profile, smaller carbon footprint, higher yields, and quick scalability with minimum reaction optimization; thus it supports rapid iteration for hit-to-lead optimization. Another approach has been described in Alam et al. [Tetrahedron Lett. 2016 57:2059] and used to scale-up analogs. The analog library and SAR disclosed herein can enable systematic investigation of the importance of increased Gp130 signaling in AD and elucidate the role of small molecule Gp130 agonists for neuroprotection.

Alzheimer's disease (AD) is the most prevalent age-related dementia and currently approved therapeutics provides only temporary symptomatic relief. Therefore new approaches to therapeutic development are urgently needed. Neuronal cell death is a key feature of AD pathology and factors leading to neuronal loss are many and not completely elucidated [Pepeu et al., 2017, Brain Res., 1670:173].

Compounds 2-8 were rationally designed to a gain better under-standing of how they activate Gp130, we performed binding studies using the Swissdock and Gold programs; this revealed domains D4 to D6 as a potential high affinity binding site in the Gp130 extracellular region for Compound 2(FIG. 1) and Compounds 3-8 and SC144 (FIGS. 6-12, respectively). A known Gp130 antagonist, SC144, was also modeled in parallel to investigate the specificity of the compounds. SC144 was found to potentially have high affinity binding for the same domain. The ClusPro docking server was used to model the interactions between HN and the extracellular domains of Gp130 [Comeau et al., 2004, J. Nucleic Acids Res., 32:W96]; this also revealed domains D4-D6 as a potential high affinity binding sites in the Gp130 extracellular region. The active compounds and the Gp130 antagonist SC144 bound to D4-D6 of Gp130 receptor (FIG. 1) revealing that they could act as small molecule mimetics of HN.

Figure 4:
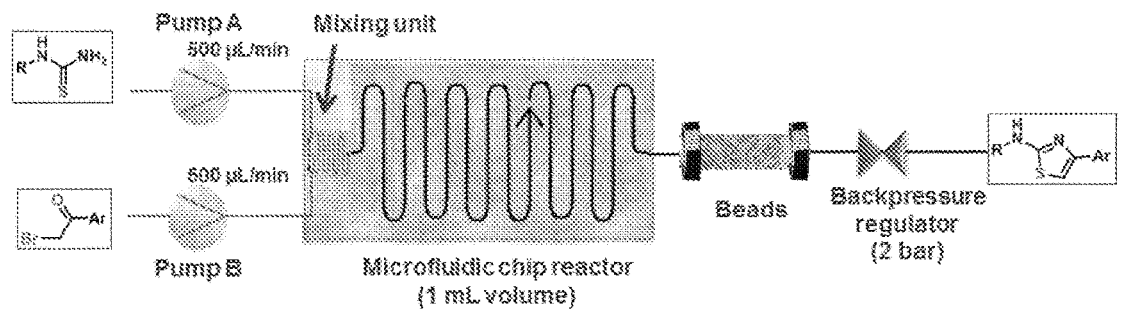
FIG. 4. Microfluidic reactor for syntheses of compounds disclosed in accordance with the present disclosure.
Figure 5:
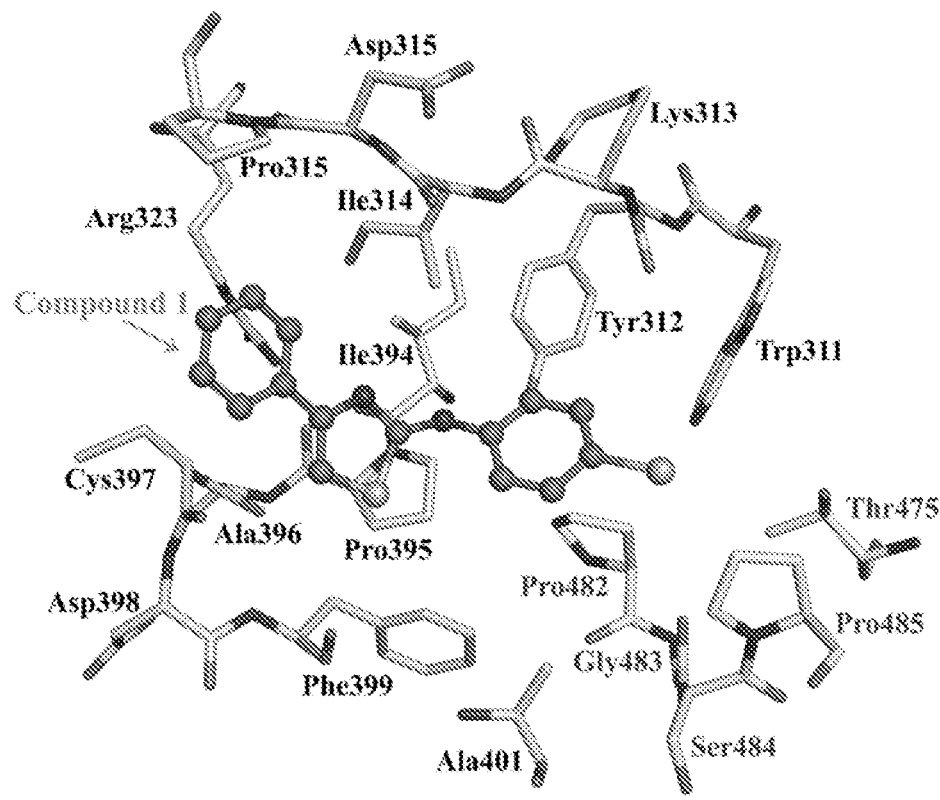
FIG. 5. Binding mode for compound 1 at the interface between the D4 and D5 domains of gp130. Primarily the interactions are hydrophobic in nature. Compound 1 is shown in ball and stick representation. The gp130 D4 and D5 residues within 5 Å radius of compound 1 at the binding site are shown in stick representation. The carbon atoms are shown in dark gray and light gray for compound 1 and gp130 D4-D5 residues, respectively. The binding mode fitness score and the AG values for the compound 1 are −1500.55 and −7.22 kcal/mol, respectively.
Figure 6:
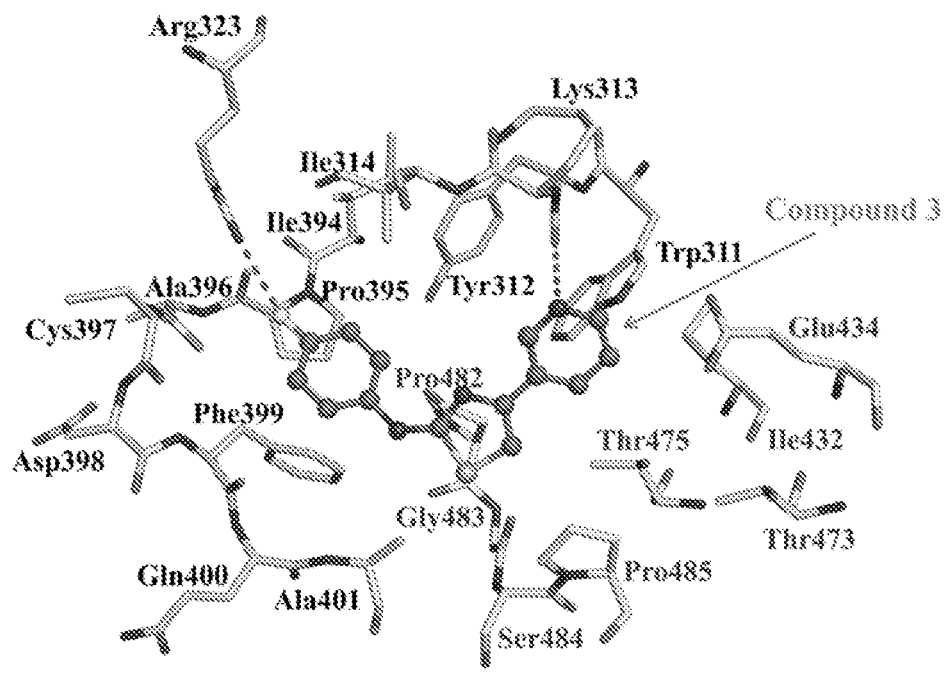
FIG. 6. Binding mode for compound 3 at the interface between the D4 and D5 domains of gp130. Primarily the interactions are hydrophobic in nature. Compound 3 is shown in ball and stick representation. The gp130 D4 and D5 residues within 5 Å radius of compound 3 at the binding site are shown in stick representation. The carbon atoms are shown in dark gray and light gray for compound 3 and gp130 D4-D5 residues, respectively. The binding mode fitness score and the AG values for the compound 3 are −1514.15 and −7.55 kcal/mol, respectively.
Figure 7:
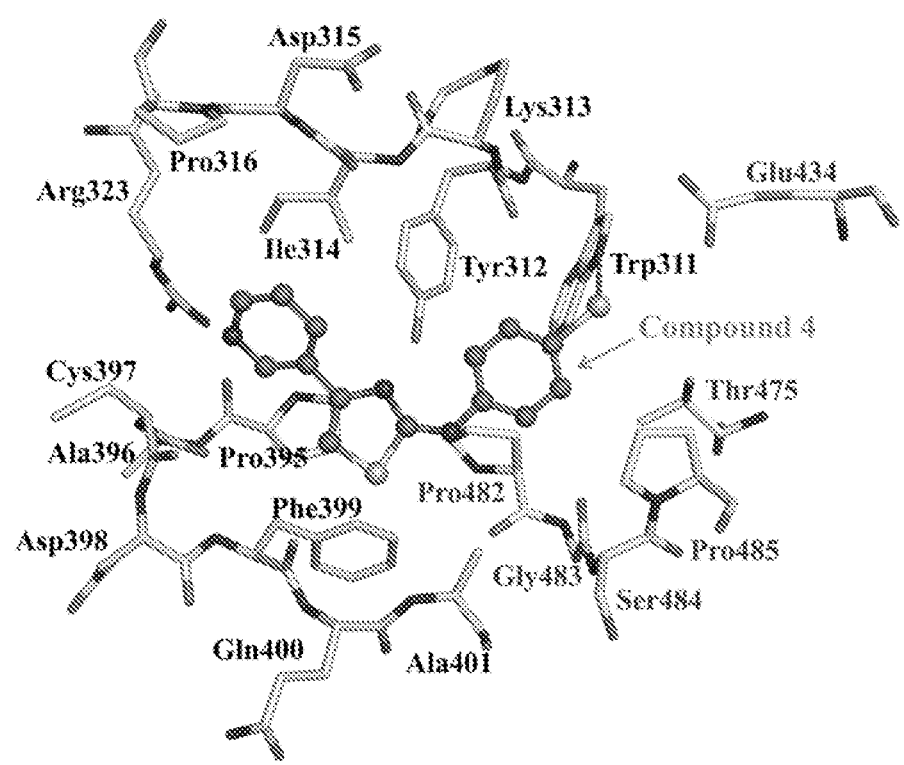
FIG. 7. Binding mode for compound 4 at the interface between the D4 and D5 domains of gp130. Primarily the interactions are hydrophobic in nature. Compound 4 is shown in ball and stick representation. The gp130 D4 and D5 residues within 5 Å radius of compound 4 at the binding site are shown in stick representation. The carbon atoms are shown in dark gray and light gray for compound 4 and gp130 D4-D5 residues, respectively. The binding mode fitness score and the AG values for the compound 4 are −1509.6 and −7.30 kcal/mol, respectively.
Figure 8:
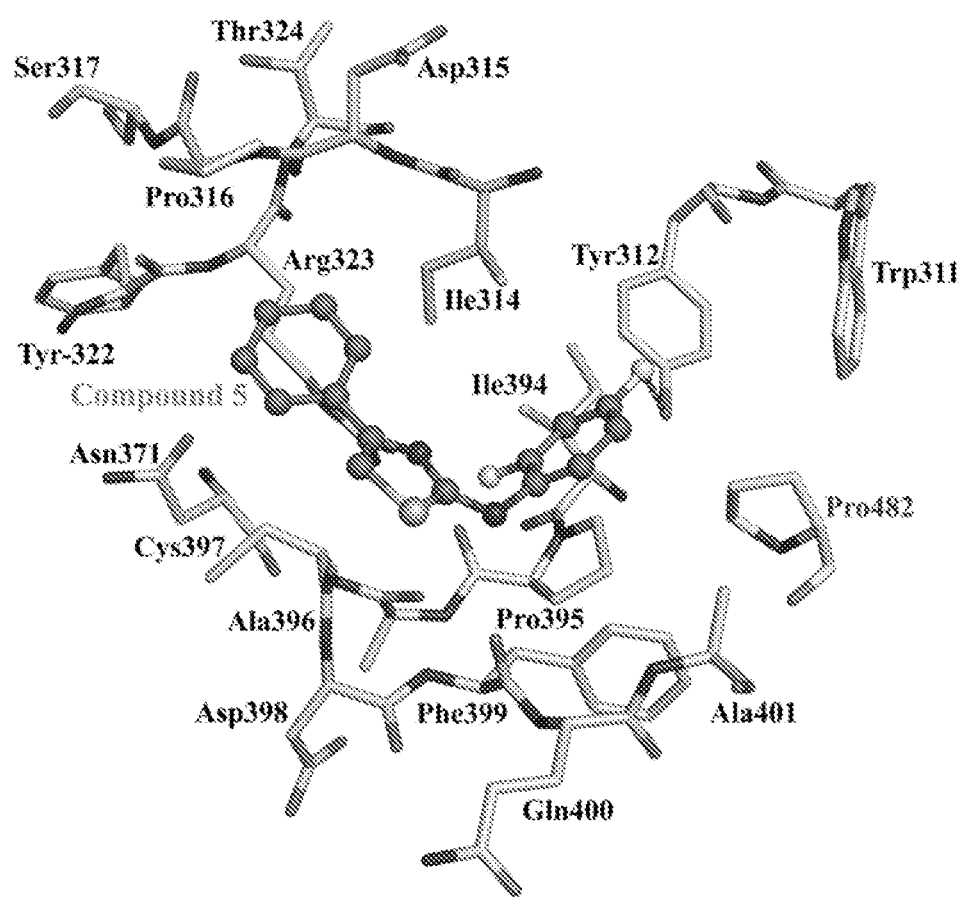
FIG. 8. Binding mode for compound 5 at the interface between the D4 and D5 domains of gp130. Primarily the interactions are hydrophobic in nature. Compound 5 is shown in ball and stick representation. The gp130 D4 and D5 residues within 5 Å radius of compound 5 at the binding site are shown in stick representation. The carbon atoms are shown in dark gray and light gray for compound 5 and gp130 D4-D5 residues, respectively. The binding mode fitness score and the AG values for the compound 5 are −1497.47 and −7.19 kcal/mol, respectively.
Figure 9:
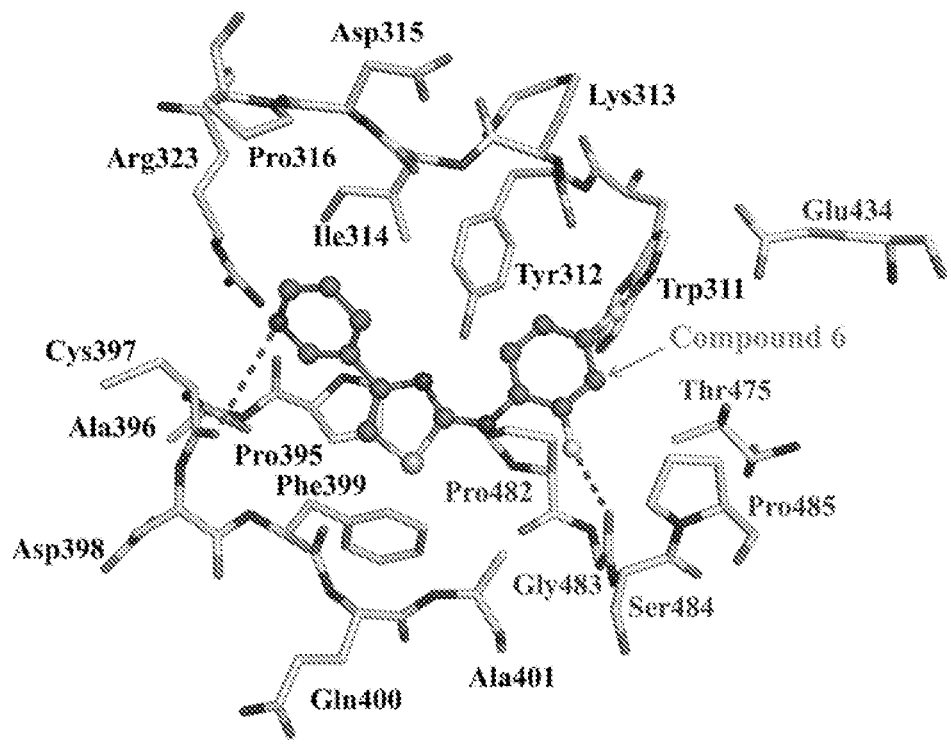
FIG. 9. Binding mode for compound 6 at the interface between the D4 and D5 domains of gp130. Primarily the interactions are hydrophobic in nature. Compound 6 is shown in ball and stick representation. The gp130 D4 and D5 residues within 5 Å radius of compound 6 at the binding site are shown in stick representation. The carbon atoms are shown in dark gray and light gray for compound 6 and gp130 D4-D5 residues, respectively. The binding mode fitness score and the AG values for the compound 6 are −1502.49 and −7.21 kcal/mol, respectively.
Figure 10:
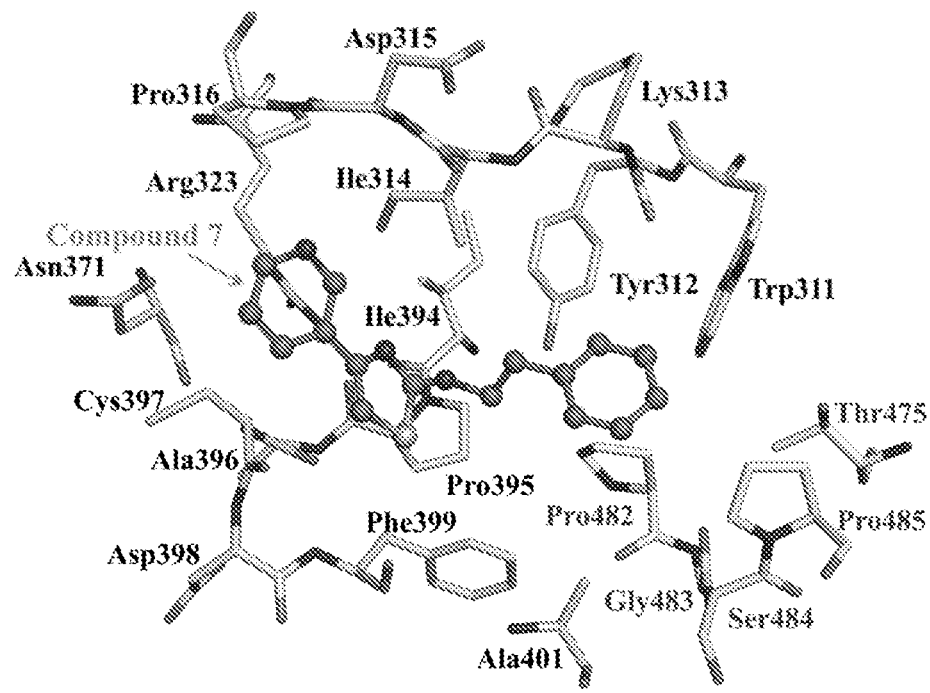
FIG. 10. Binding mode for compound 7 at the interface between the D4 and D5 domains of gp130. Primarily the interactions are hydrophobic in nature. Compound 7 is shown in ball and stick representation. The gp130 D4 and D5 residues within 5 Å radius of compound 7 at the binding site are shown in stick representation. The carbon atoms are shown in dark gray and light gray for compound 7 and gp130 D4-D5 residues, respectively. The binding mode fitness score and the AG values for the compound 7 are −1519.72 and −7.57 kcal/mol, respectively.
Figure 11:
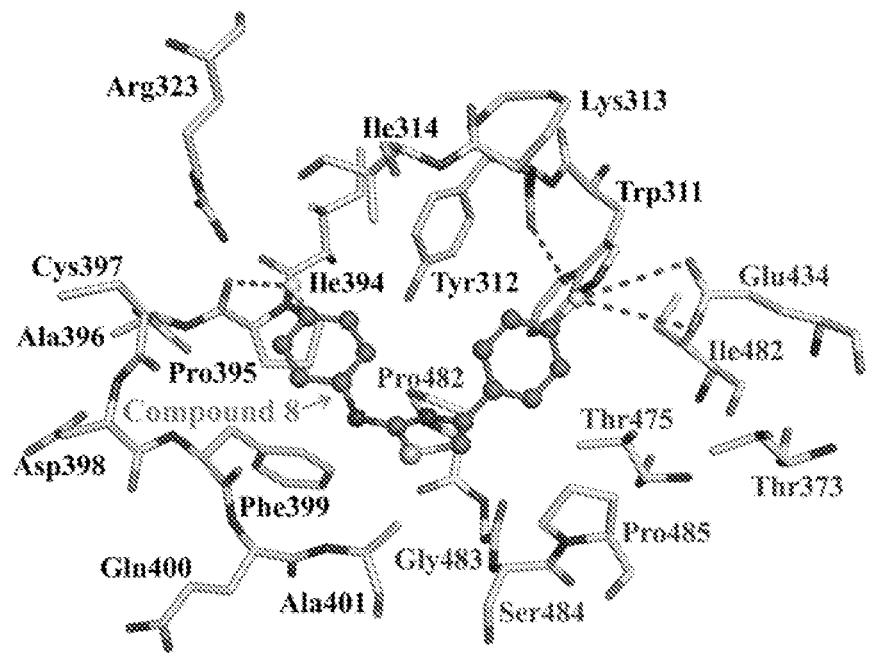
FIG. 11. Binding mode for compound 8 at the interface between the D4 and D5 domains of gp130. Primarily the interactions are hydrophobic in nature. Compound 8 is shown in ball and stick representation. The gp130 D4 and D5 residues within 5 Å radius of compound 8 at the binding site are shown in stick representation. The carbon atoms are shown in dark gray and light gray for compound 8 and gp130 D4-D5 residues, respectively. The binding mode fitness score and the AG values for the compound 8 are −1507.46 and −7.21 kcal/mol, respectively.
Figure 12:
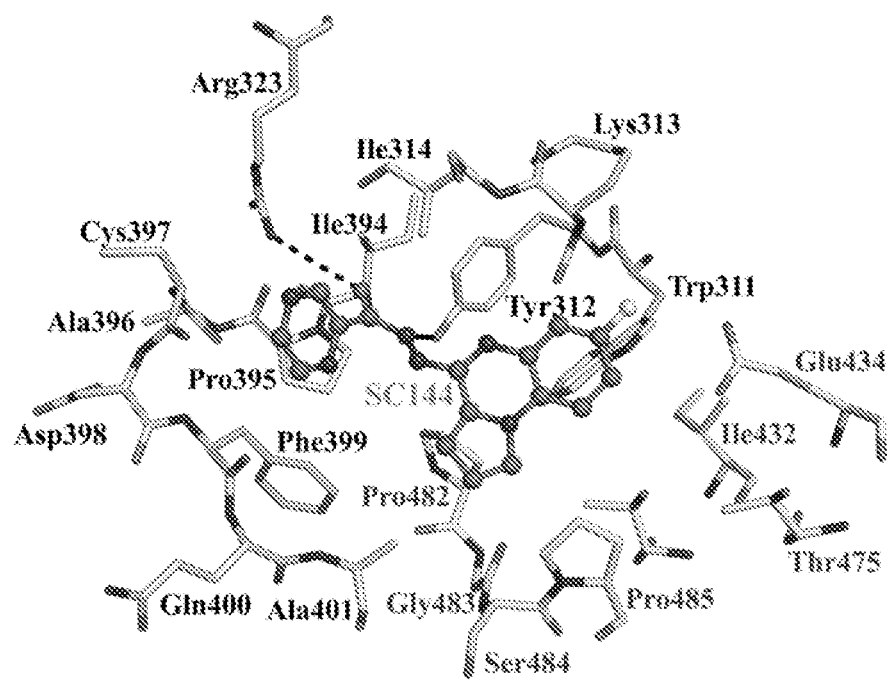
FIG. 12. Binding mode for SC144 at the interface between the D4 and D5 domains of gp130. Primarily the interactions are hydrophobic in nature. SC144 is shown in ball and stick representation. The gp130 D4 and D5 residues within 5 Å radius of SC144 at the binding site are shown in stick representation. The carbon atoms are shown in dark gray and light gray for compound SC144 and gp130 D4-D5 residues, respectively. The binding mode fitness score and the AG values for the SC144 are −1440.52 and −7.67 kcal/mol, respectively.
Figure 13:
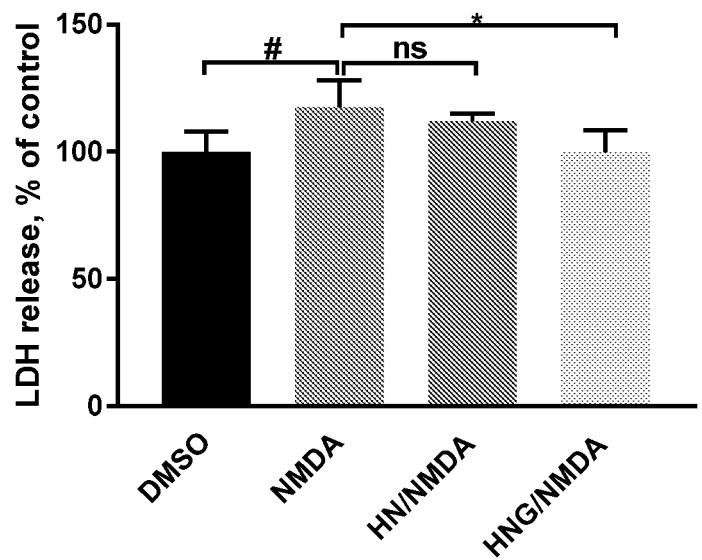
FIG. 13. Effect of HN and HNG on NMDA triggered LDH release in cultured hippocampal neurons. Each bar represents mean±SEM of four independent observations. Statistical significance was at $P<0.05$. One-way ANOVA with NMDA as control for comparison with HN/NMDA and HNG/NMDA gave F=5.11 and P=0.03. Dunnett's multiple comparisons test reveals NMDA vs. HN/NMDA non-significance at P=0.53; and NMDA vs. HNG/NMDA significance at P=0.02. Unpaired two-tailed Student's t-test reveals DMSO vs. NMDA significance at P=0.03, t=2.68.

Compound 1 and the analogs we synthesized belongs to 2-aminothiazoles family of compounds, and while many methods have been reported to synthesize 2-aminothiazoles, including solution [Bailey et al., 1996, Bioorg. Med. Chem. Lett., 6(12):1409], solid phase synthesis [Kazzouli et al., 2002, Tetrahedron Lett., 43(17): 3193], microwave promoted synthesis [Kabalka et al., 2006, Tetrahedron Lett., 47(29):5171], and a tandem one-pot aqueous phase synthesis [Madhav et al., 2012, Tetrahedron Lett., 53(30): 3835]; our method of 2-aminothiazoles preparation using 2-bromo-1-phenylethan-1-one (and its derivatives) and 1-(4-bromophenyl)thiourea (and its derivatives) through Hantzsch condensation [Hantzsch et al., 1887, Ber. Dtsch. Chem. Ges., 20:3118] in a microfluidic reactor without the use of a catalyst is unprecedented. We used state-of-the-art flow-chemistry [Alam et al., 2016, Tetrahedron Lett., 57(19): 2059] for our exploratory medicinal chemistry and structure-activity relationship (SAR) campaign. Microfluidic flow chemistry facilitated rapid syntheses of new analogs using a green chemistry approach with a cleaner reaction profile, smaller carbon footprint, higher yields, and quick scalability with minimum reaction optimization enabling us to gain chemical insights quickly into the optimal SAR for Gp130 agonism and neuroprotection. The reactions are rapid, proceeding to completion in a minute and products are obtained in good-to-excellent yields after a simple workup followed by flash silica gel column chromatography. As a result of these efforts, we report the synthesis of N-(2,4-difluorophenyl)-4-(pyridin-3-yl)thiazol-2-amine (compound 6) for the first time. The chemical synthesis of the compound 1 began from commercially available 2-bromo-1-phenylethan-1-one and 1-(4-bromophenyl)thiourea. They were premixed in a separate vial and were pumped through a preheated glass microfluidic reactor (Syrris Asia Flow Chemistry Module) at a 500 μL/min flow rate with a one minute residence time in the reactor using a Syrris Asia pump (FIG. 4 and Scheme 1) to afford compound 1 from the output stream after. Other compounds were synthesized (Table 2) by similarly pumping corresponding starting material through the preheated glass microfluidic reactor (FIG. 4 and Scheme 1).

With a number of analogs in hand, we next sought to demonstrate that a small molecule Gp130 agonist such as compound 2 (Table 2) and/or its analogs can confer, and perhaps even improve upon, the cellular protection provided by HN or HNG.

In this study, the cytotoxicity of NMDA was quantified by measuring the activity of lactate dehydrogenase (LDH) released from the cultured neurons into the medium and confirmed by living cell density analysis using calcein staining. Our results showed that NMDA treatment (100 µM, 2.5 h) damaged cultured neurons and thus triggered over-release of LDH (Table 2 and FIG. 15). LDH level in the NMDA treatment group was about 26% higher than that in the DMSO control. MK-801, a noncompetitive antagonist of NMDA receptor, was used as a control [Wong et al., 1986, Proc. Natl. Acad. Sci. U.S.A., 83(18):7104]. As shown in Table 2 and FIG. 15, the addition of MK-801 significantly reduced the release of LDH from NMDA-treated neurons by 43%. We evaluated different batches of HN from different vendors in our assay and only one of them was active and exhibited protection against NMDA-evoked excitotoxicity (data not shown). Neither HN itself nor the compounds had effect on neurons, which were not treated with NMDA. However, the release of LDH was significantly inhibited in NMDA-treated neurons when they were pretreated with compounds 1-8 for 16 h. While the level of LDH release was decreased by 20% of the NMDA-treated control with our initial lead 1 pre-treatment we found a greater decrease of LDH release by HN mimetic analogs 2-8 at 10 µM as shown in Table 2. The greatest decrease was seen with compounds 2, 4, 5 and 8 and this was similar to what was observed with MK-801.

Figure 15:
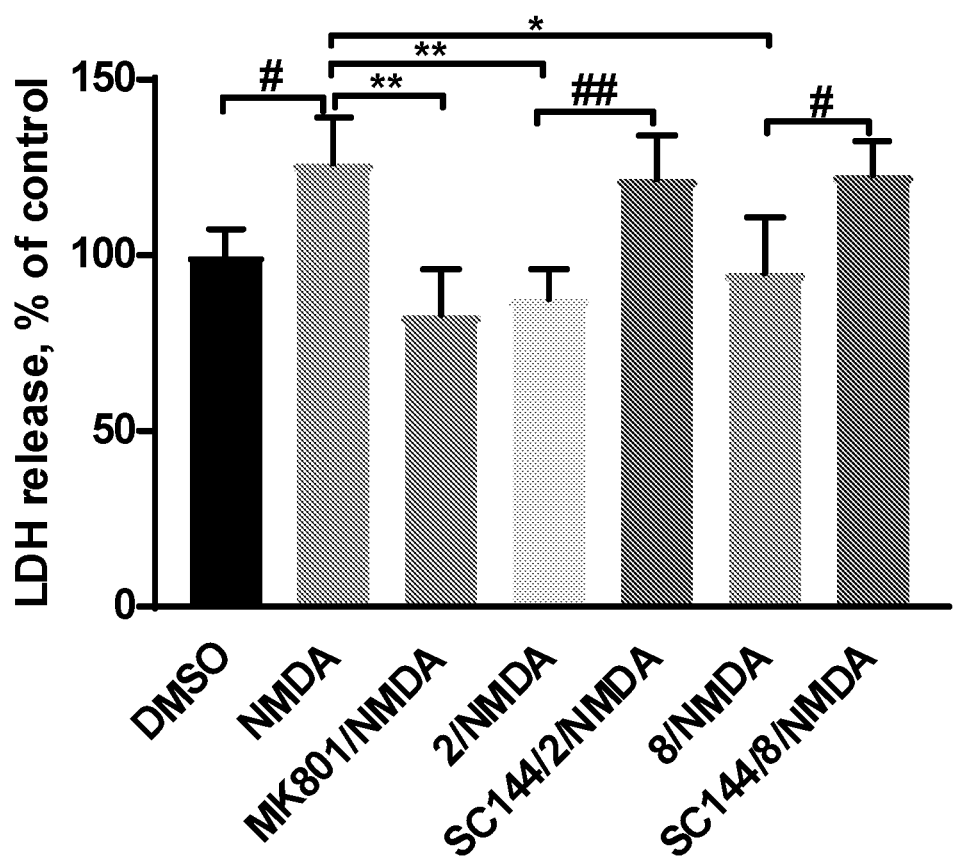
FIG. 15. Effect of co-treatment of gp130 antagonist, SC144, MK801 and compounds 2 and 8 on NMDA-triggered LDH release in cultured hippocampal neurons. NMDA increased LDH release (bar 2), and both MK801 and compound 2 rescued the LDH increase (bars 3 and 4, respectively). Antagonist SC144 prevented compound 2 rescue (bar 5). Compound 8 also rescued LDH and SC144 prevented this rescue (bars 6 and 7, respectively). Each bar represents mean±SEM of four independent observations. Statistical significance was at $P<0.05$. One-way ANOVA with NMDA as control for comparison with MK801/NMDA, 2/NMDA and 8/NMDA gave P=0.002.
Figure 16A:
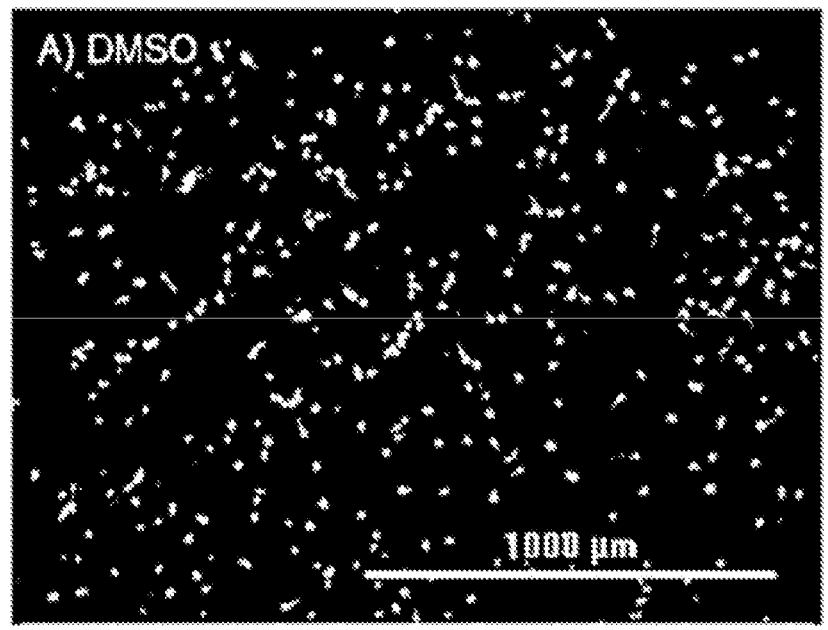
FIGS. 16A-16D. Effect of compound 2 on density of hippocampal neurons under NMDA-induced toxicity. Fluorescent microscopy was used to show representative calcein staining, and cellular density of each group.
Figure 16B:
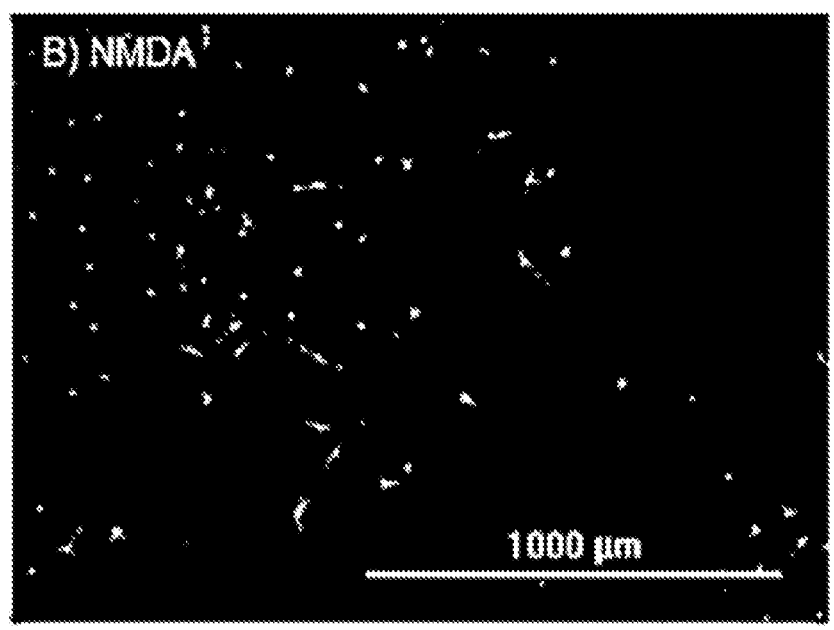
Figure 16C:
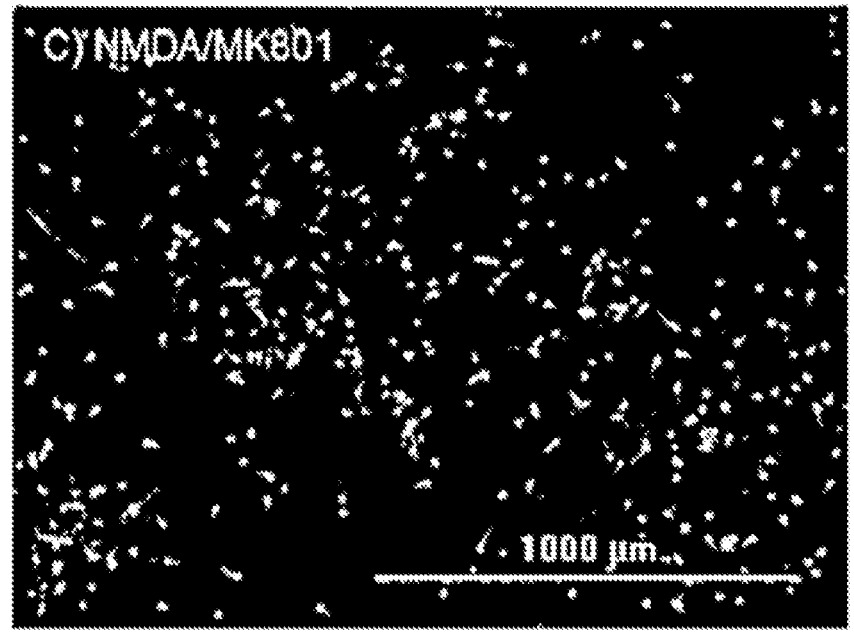
Figure 16D:
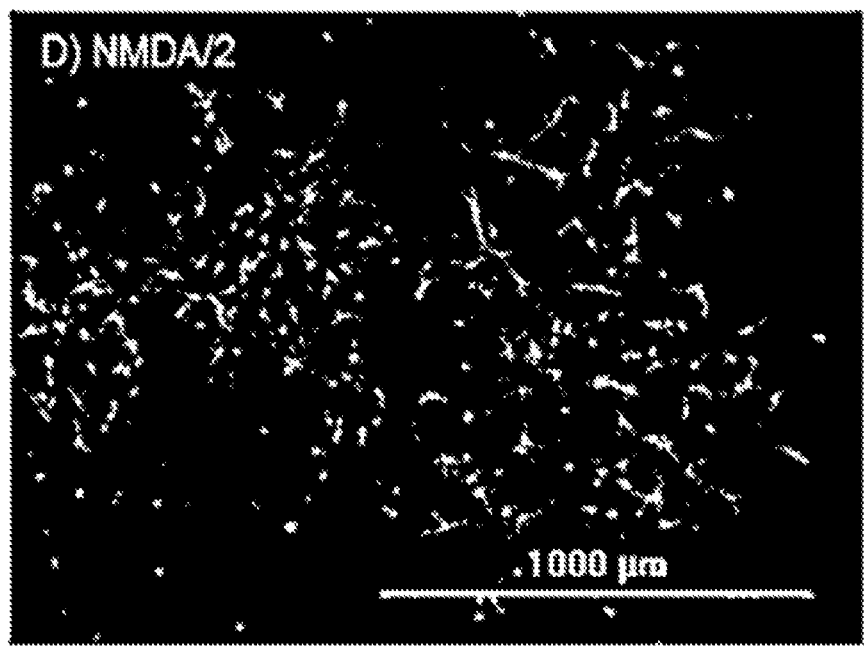

To demonstrate that compounds 2-8 were providing protection through interaction with Gp130, we pretreated the primary neurons with SC-144, a known Gp130 antagonist followed by treatment with either compound 2 or 8. SC-144 pretreatment abated the protection provided by compounds 2 or 8 against NMDA-evoked excitotoxicity (FIG. 15).

Figure 14:
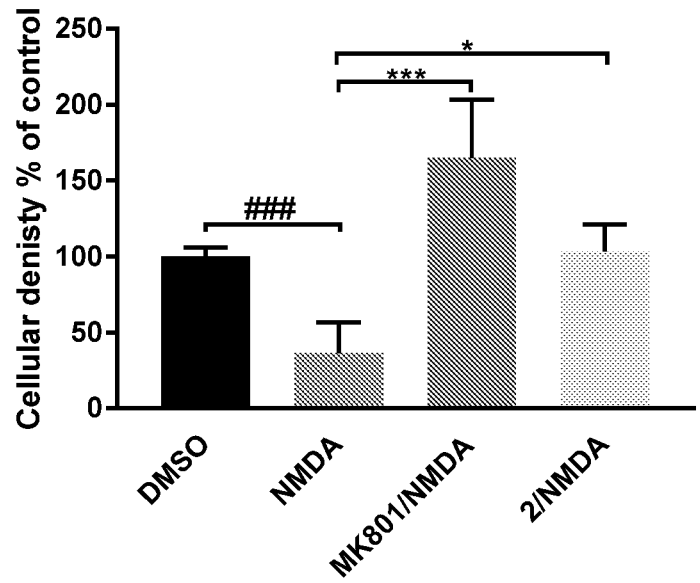
FIG. 14. Effect of MK801 and 2 on density of living neurons under NMDA-induced excitotoxicity. Each bar represents mean±SEM of four independent observations. Statistical significance was at $P<0.05$. One-way ANOVA with NMDA as control for comparison with MK801/NMDA and 2/NMDA gave F=22.26 and P=0.0003. Dunnett's multiple comparisons test reveals NMDA vs. MK801/NMDA significance at P=0.0002; and NMDA vs. 2/NMDA significance at P=0.0128. Unpaired two-tailed Student's t-test reveals DMSO vs. NMDA significance at P=0.0009, t=6.043.

Calcein staining was employed to evaluate the density of living neurons. A highly lipophilic non-fluorescent and cell permeable compound, calcein-acetoxymethyl ester (calcein-AM) was used for staining. Calcein-AM can be converted by intracellular esterases into calcein, an anionic fluorescent form, only labeling viable cells, and thus provides both morphological and functional information about undamaged cells. NMDA (100 µM, 2.5 h) alone induced a significant decrease in neuronal survival—more than half of the cells died. As an additional control, we have evaluated MK-801, a non-competitive antagonist of NMDA receptor, in parallel with compounds 1-8. With MK-801 pretreatment, the density of NMDA-treated neurons was similar to the DMSO-only control, which indicated that the toxicity was induced by NMDA receptor activation. There was no difference in density of living neurons between the compound 2 group and the DMSO-only control group, suggesting that compound 2 (10 µM) could reduce NMDA-triggered toxicity similar to the direct antagonist, MK-801 (FIG. 14 and FIG. 16).

Figure 17:
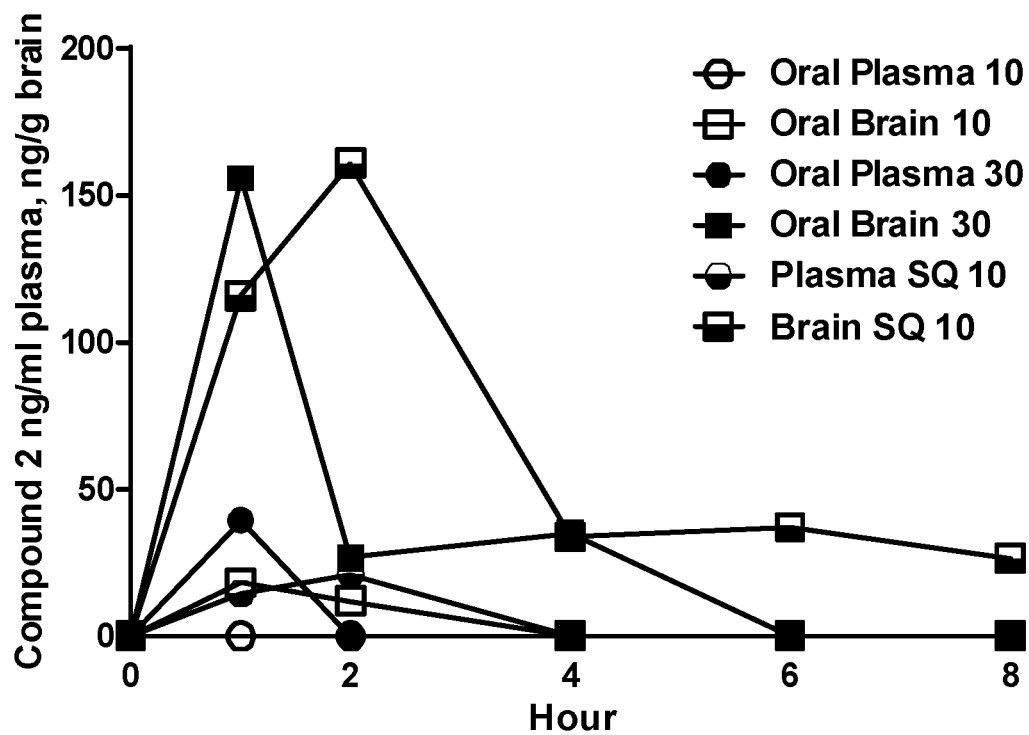
FIG. 17. Compound 2 levels in mice brain and plasma. Mice were dosed orally at 10 or 30 mg/kg, or injected subcutaneously (SQ) at 10 mg/kg. Compound 2 is orally bioavailable at a dose of 30 mg/kg with a $C_{max}$~0.57 µM level in the brain at 1 h post dose.

Our determination of the neuroprotective effects of the compound 2 and its binding site on Gp130 suggest its potential as an AD therapeutic. Since any potential therapeutic for AD needs to cross the blood-brain barrier (BBB), we further evaluated the brain permeability of Gp130 compound 2 in mice. Mice were dosed orally at 10 or 30 mg/kg, or injected subcutaneously (SQ) at 10 mg/kg, and euthanized after 1, 2, 4, 6, and 8 hours post-dose. We found that Cmax for brain at 2 h for SQ delivery at 10 mg/kg was 161 ng/g whereas Cmax for brain at 1 h for oral delivery at 10 mg/kg was about 18 ng/g. Dosing at 30 mg/kg orally resulted in a 156 ng/g (0.57 µM) Cmax for brain at 1 h post dose (FIG. 17). The brain to plasma ratio for compound 2 was ~4:1 for oral 30 mg/kg; and ~7.5:1 for 10 mg/kg SQ injection. Based on the oral brain levels of compound 2 we will conduct proof-of-concept testing in a mouse model of NMDA-induced toxicity in future studies.

In the present study, our results show that small molecule humanin mimetics provide neuroprotection from excitatory neurotoxicity induced by NMDA in the primary hippocampal neurons, and it does so through interaction with Gp130 to induce downstream signaling. Through computer modeling, we have shown that compounds 1-8 and HN interact with the same domain of Gp130. The small molecule HN mimetics of the present disclosure are likely candidates as potential therapeutics for AD than HN itself, since HN, due to its peptidic structure, presents challenges in its development as a therapeutic. Although some efficacy of HN derivative HNG has been seen in murine models of AD after intranasal [Niikura et al., 2011, PLoS One, 6(1):e16259] delivery and intraperitoneal injection [Zhang et al., 2012, Pharmacol. Biochem. Behav., 100(3): 361], these delivery methods are not readily adaptable to human patients. In rats, after intraperitoneal injection (IP) of HNG, levels were found to be highest in plasma, detectable in liver, but undetectable in brain, indicating poor brain-penetrance [Chin et al., 2013, Endocrinology, 154(10): 3739]. Therefore, from a therapeutic standpoint, a small molecule Gp130 agonist mimetic of HN represents an attractive modality for rapid development and ease of delivery. As reported here, our pharmacokinetic analysis of compound 2 in mice established that it is orally bioavailable at a dose of 30 mg/kg with a Cmax 0.57 M. By identifying a small molecule HN mimetic, we have generated a promising tool for in vivo proof-of-concept testing of neuroprotection through Gp130 agonism. Further efforts will be made towards making new analogs to explore SAR and expand our library of small molecule HN mimetics, and attention will be paid to unveil the underlying Gp130 downstream signaling mechanism. Such compounds may be neuroprotective and potentially lead to a new pharmacological class of AD therapeutic agents. An efficacious compound from this class may be used alone or in combination with other anti-AD drugs.

Materials.

Anhydrous grade solvents were purchased from Sigma-Aldrich Inc. (St. Louis, Mo.) and from Fisher Scientific. Most of the chemical reagents were purchased from Sigma-Aldrich and used without further purification. N-methyl-D-aspartate (NMDA) was purchased from Sigma-Aldrich. 2-Bromo-1-phenylethan-1-one, 1-(4-bromophenyl)thiourea, 1-(4-florophenyl)thiourea, 1-(2,4-diflorophenyl)thiourea, 2-bromo-1-(4-fluorophenyl)ethan-1-one, and 1-phenethylthiourea were purchased from TCI America. 2-Bromo-1-(pyridin-3-yl)ethan-1-one hydrochloride was purchased from Oxchem Corporation. Humanin (HN) and humanin analog (HNG) batches were purchased from Anaspec and Tocris Bioscience. SC144 hydrochloride and (+)-MK801 maleate were purchased from Tocris Bioscience. Analytical thin layer chromatographic separations were carried out on silica gel (60 Å particle size, 250 Å thickness, F-254, Silicycle) coated glass plates. Spots were visualized by exposure to UV light.

NMR spectra were recorded using a 400 MHz Bruker spectrometer. Chemical shifts are reported in parts per million (ppm, $\delta$) relative to residual $^1$H resonance of the solvent $CDCl_3$ and $C_2D_6SO$ at 7.26 ppm and 2.50 ppm, respectively. $^{13}$C NMR chemical shifts are reported relative to the central line of $CDCl_3$ and $C_2D_6SO$ at 77.16 ppm and 39.49 ppm, respectively. Mass Spectrometry Instrumentation was made available through the support of Dr. Greg Khitrov at the University of California, Los Angeles Molecular Instrumentation Center—Mass Spectrometry Facility in the Department of Chemistry. High-resolution DART-MS spectra were collected on a Thermo Exactive Plus MSD (Thermo Scientific) equipped with an ID-CUBE ion source and a Vapur Interface (IonSense). Both the source and MSD were controlled by Excalibur v. 3.0. The analyte was spotted onto OpenSpot sampling cards (IonSense) using chloroform as the solvent. Ionization was accomplished using helium (He) plasma with no additional ionization agents.

Animal Compliance.

The C57B16J mice used for pharmacokinetic analysis and to generate embryos for primary culture were purchased from Jackson Laboratories (Bar Harbor, Me.) and were bred and maintained in the Department of Laboratory Animal Medicine (DLAM) at UCLA. All animal experiments were conducted according to the guidelines and approval of the UCLA Animal Research Committee (ARC) under an approved protocol.

EXAMPLES

Example 1. Preparation of N-(4-bromophenyl)-4-phenylthiazol-2-amine (PA1, Compound 1), N-(4-fluorophenyl)-4-phenylthiazol-2-amine (PA2, Compound 2), N-(4-fluorophenyl)-4-(pyridin-3-yl)thiazol-2-amine (PA3, Compound 3), and N-(4-bromophenyl)-4-(pyridin-3-yl)thiazol-2-amine (PA5, Compound 4)

Scheme 1 is a chemical reaction scheme useful for preparation of N-(4-bromophenyl)-4-phenylthiazol-2-amine (PA1), N-(4-fluorophenyl)-4-phenylthiazol-2-amine (PA2), N-(4-fluorophenyl)-4-(pyridin-3-yl)thiazol-2-amine (PA3), and N-(4-bromophenyl)-4-(pyridin-3-yl)thiazol-2-amine (PA5).

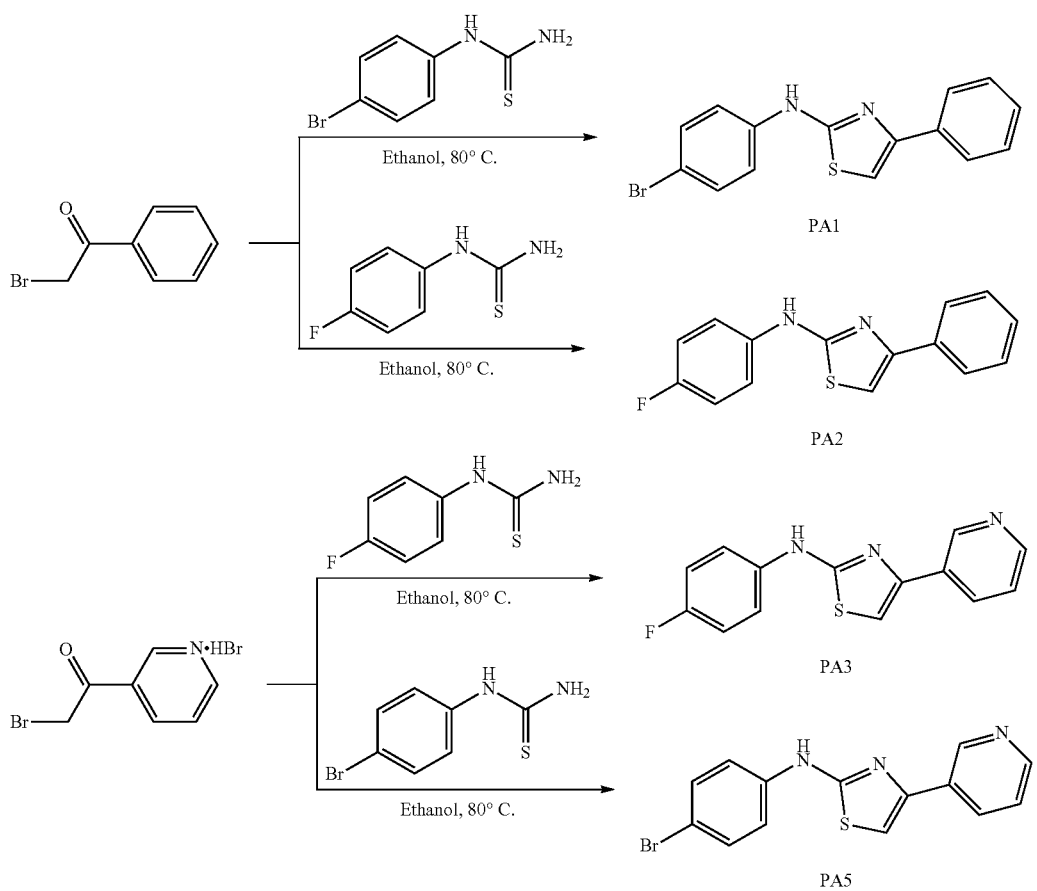

Scheme 1.

Referring to Scheme 1, 2-bromo-1-phenylethan-1-one (1.0 equivalent, 0.5 mmol) and 1-(4-fluorophenyl)thiourea (1.0 equivalent, 0.5 mmol) were premixed in 2.5 mL of ethanol each in a separate vial. The mixture was pumped through a preheated glass microfluidic reactor (Syrris Asia Flow Chemistry Module) at a predetermined flow rate to have the desired residence time using Syrris Asia pump. The outcome was collected in a flask and concentrated under reduced pressure. The crude was dissolved in 10 mL ethyl acetate washed with 2×10 mL satd. NaHCO₃. The organic phase was combined, dried MgSO₄ and concentrated under reduced pressure. The crude obtained was purified using prepacked silica cartridge on Teledyne CombiFlash Rƒ200. Elution with 10:90 hexane-ethyl acetate afforded PA2 in 97% yield. The product was obtained as a colorless powder ¹H NMR (CDCl₃) δ 8.16 (s, 1H), 7.86-7.74 (m, 2H), 7.45-7.22 (m, 5H), 7.04-6.94 (m, 2H) and 6.78 (s, 1H); ¹³C NMR (101 MHz, CDCl₃) δ 165.99, 160.25, 157.84, 151.52, 136.71, 136.68, 134.60, 128.73, 128.07, 126.29, 121.10, 121.02, 116.28, 116.05 and 101.67. The same methodology was used to synthesize other three compounds PA1, PA3 and PA5. For PA1, The product was obtained as a colorless powder, Yield 98% (162 mg). ¹H NMR (CDCl₃) δ 8.35 (s, 1H), 7.87-7.78 (m, 2H), 7.42-7.29 (m, 5H), 7.23-7.16 (m, 2H) and 6.83 (s, 1H); ¹³C NMR (101 MHz, CDCl₃) δ 164.56, 151.46, 139.52, 134.46, 132.30, 128.79, 128.17, 126.32, 119.85, 115.19 and 102.15. For PA3, The product was obtained as a pale yellow powder, Yield 94% (128 mg). ¹H NMR (C₂D₆SO) δ 10.36 (s, 1H), 9.14 (dd, J=2.3, 0.8 Hz, 1H), 8.51 (dd, J=4.8, 1.6 Hz, 1H), 8.25 (dt, J=8.0, 1.9 Hz, 1H), 7.81-7.69 (m, 2H), 7.52 (s, 1H), 7.55-7.41 (m, 1H) and 7.26-7.14 (m, 2H); ¹³C NMR (C₂D₆SO) δ 163.65, 158.09, 155.73, 148.42, 147.12, 146.96, 137.57, 137.54, 132.76, 130.07, 123.70, 118.51, 118.43, 115.64, 115.42 and 104.51. For PA5, The product was obtained as a yellowish powder, Yield 95% (158 mg). ¹H NMR (C₂D₆SO) δ 10.49 (s, 1H), 9.14 (dd, J=2.3, 0.9 Hz, 1H), 8.52 (dd, J=4.8, 1.6 Hz, 1H), 8.26 (ddd, J=8.0, 2.3, 1.7 Hz, 1H), 7.76-7.68 (m, 2H) and 7.59-7.38 (m, 4H); ¹³C NMR (C₂D₆SO) δ 163.16, 148.47, 147.21, 146.98, 140.31, 132.80, 131.72, 130.00, 124.78, 123.71, 118.83, 112.45 and 105.03.

Example 2. Preparation of N-(2,4-difluorophenyl)-4-phenylthiazol-2-amine (PA6, Compound 5), N-(2,4-difluorophenyl)-4-(pyridin-3-yl)thiazol-2-amine (PA7, Compound 6), N-phenethyl-4-(pyridin-3-yl)thiazol-2-amine (PAJ2, Compound 7), and N,4-bis(4-fluorophenyl)thiazol-2-amine (PA14, Compound 8)

2-bromo-1-phenylethan-1-one (1.0 equivalent, 0.5 mmol) and 1-(4-bromophenyl)thiourea (1.0 equivalent, 0.5 mmol) were premixed in 2.5 mL of ethanol each in a separate vial. The solution was pumped through a preheated (80° C. and 2 bar pressure) glass microfluidic reactor (Syrris Asia Flow Chemistry Module) at a 500 µL/min flow rate from two pumps to have the desired residence time of one minute in the glass microfluidic reactor. The output of the reactor was passed through a column packed with ion exchange resin (Amberlite IRA-900) to quench the hydrochloride produced as a side product and to prevent the clogging of back pressure regulator due to salt accumulation otherwise. The output was collected in a flask and concentrated under reduced pressure. The crude was suspended in 20 mL dichloromethane and washed with 2×10 mL satd. NaHCO₃. The organic phase was combined, dried MgSO₄ and concentrated under reduced pressure. The crude obtained was purified using prepacked silica cartridge on Teledyne CombiFlash Rƒ200. Elution with 10:90 hexane-ethyl acetate afforded PA1 in 98% yield. The same methodology was used to synthesize other four compounds PA6, PA7, PA12, and PA14. For PA6, The product was obtained as a pale yellow powder, Yield 96% (138 mg). ¹H NMR (CDCl₃) δ 8.28-8.17 (m, 1H), 7.88-7.81 (m, 2H), 7.45-7.39 (m, 2H), 7.36-7.28 (m, 1H), 6.99-6.88 (m, 2H) and 6.86 (s, 1H); ¹³C NMR (101 MHz, CDCl₃) δ 163.59, 151.68, 134.47, 128.80, 128.18, 126.22, 120.24, 111.53, 111.32, 104.27, 104.04, 103.78 and 102.62. For PA7, The product was obtained as a pale yellow powder, Yield 92% (133 mg). ¹H NMR (C₂D₆SO) δ 10.11 (d, J=1.6 Hz, 1H), 9.09 (dd, J=2.2, 0.9 Hz, 1H), 8.58-8.42 (m, 2H), 8.22 (ddd, J=7.9, 2.3, 1.6 Hz, 1H), 7.52 (s, 1H), 7.44 (ddd, J=8.0, 4.8, 0.9 Hz, 1H), 7.31 (ddd, J=11.7, 8.8, 2.9 Hz, 1H) and 7.17-7.07 (m, 1H); ¹³C NMR (C₂D₆SO) δ 164.18, 148.56, 147.01, 146.97, 133.02, 130.22, 123.96, 121.23, 111.48, 111.45, 111.23, 105.83, 104.35 and 104.12; mass spectrum (APCI), m/z calcd for C₁₄H₁₀F₂N₃S (M+H)⁺ 290.0558, found 290.0550. For PA12, The product was obtained as a colorless powder, Yield 94% (132 mg). 1H NMR (C₂D₆SO) δ 9.03 (dd, J=2.3, 0.9 Hz, 1H), 8.45 (dd, J=4.8, 1.6 Hz, 1H), 8.19-8.12 (m, 1H), 7.82 (t, J=5.4 Hz, 1H), 7.40 (dd, J=8.0, 4.8, 0.9 Hz, 1H), 7.33-7.25 (m, 4H), 7.21 (d, J=5.4 Hz, 2H) and 2.91 (t, J=7.3 Hz, 2H); 13C NMR (C₂D₆SO) δ 168.82, 148.22, 147.22, 146.99, 139.55, 132.92, 130.65, 128.86, 128.52, 126.31, 123.84, 102.66, 46.25 and 34.84. For PA14, The product was obtained as a colorless powder, Yield 92% (133 mg). ¹H NMR (CDCl₃) δ 7.83-7.72 (m, 2H), 7.39-7.32 (m, 2H), 7.12-7.01 (m, 4H) and 6.72 (s, 1H); ¹³C NMR (CDCl₃) δ 165.64, 163.96, 161.50, 160.37, 157.96, 150.43, 136.48, 130.81, 127.90, 120.97, 116.41, 116.19, 115.79, 115.57 and 101.35.

Example 3. Exemplary Compounds

Exemplary compounds include those listed in Table 1 as follows.

TABLE 1

| Compounds | |
|---|---|
| 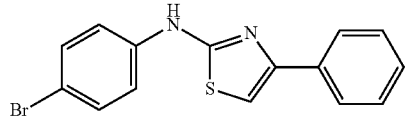 [SMILES: Brc1ccc(Nc2nc(-c3ccccc3)co2)cc1] | PA1 |
| 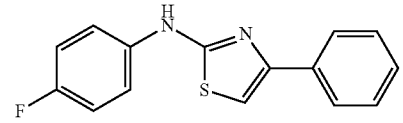 [SMILES: Fc1ccc(Nc2nc(-c3cncnc3)co2)cc1] | PA2 |
| 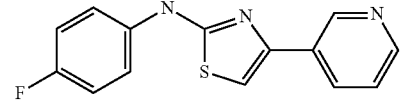 | PA3 |
| 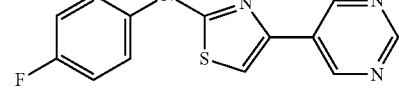 | PA4 |
| 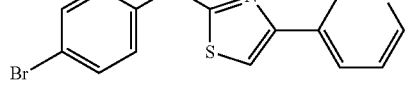 | PA5 |
| 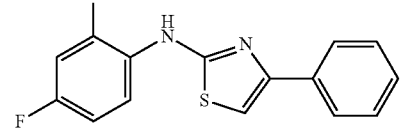 | PA6 |

TABLE 1-continued

Compounds

PA7: N-(2,4-difluorophenyl)-4-(pyridin-3-yl)thiazol-2-amine

PA8: 4-bromo-N-(4-(4-fluorophenyl)thiazol-2-yl)aniline

PA9: N-(2,4-difluorophenyl)-4-(2,4-difluorophenyl)thiazol-2-amine

PA10: N-(2,4-difluorophenyl)-4-phenylthiazol-2-amine

PA11: N-phenethyl-4-phenylthiazol-2-amine

PA12: N-phenethyl-4-(pyridin-3-yl)thiazol-2-amine

PA13: 4-(2,4-difluorophenyl)-N-(4-fluorophenyl)thiazol-2-amine

PA14: N-(4-fluorophenyl)-4-(4-fluorophenyl)thiazol-2-amine

PA15: N-(4-bromophenyl)-4-phenyloxazol-2-amine

PA16: N-(4-fluorophenyl)-4-phenyloxazol-2-amine

PA17: N-(4-fluorophenyl)-4-(pyridin-3-yl)oxazol-2-amine

PA18: N-(4-fluorophenyl)-4-(pyrimidin-5-yl)oxazol-2-amine

TABLE 2A

TABLE 2A-2B
Effect of small molecule HN mimetics on NMDA-triggered LDH release in primary hippocampal neuron culture.

TABLE 2 A

| Compound | Building blocks | | Product |
|---|---|---|---|
| | A | B | |
| RCGD423 (1) | 1-(4-bromophenyl)thiourea | 2-bromo-1-phenylethan-1-one | 4-bromo-N-(4-phenylthiazol-2-yl)aniline |
| 2 | 1-(4-fluorophenyl)thiourea | 2-bromo-1-phenylethan-1-one | N-(4-fluorophenyl)-4-phenylthiazol-2-amine |
| 3 | 1-(4-fluorophenyl)thiourea | 2-bromo-1-(pyridin-3-yl)ethan-1-one·HBr | N-(4-fluorophenyl)-4-(pyridin-3-yl)thiazol-2-amine |

TABLE 2A-continued

TABLE 2A-2B
Effect of small molecule HN mimetics on NMDA-triggered LDH release in primary hippocampal neuron culture.

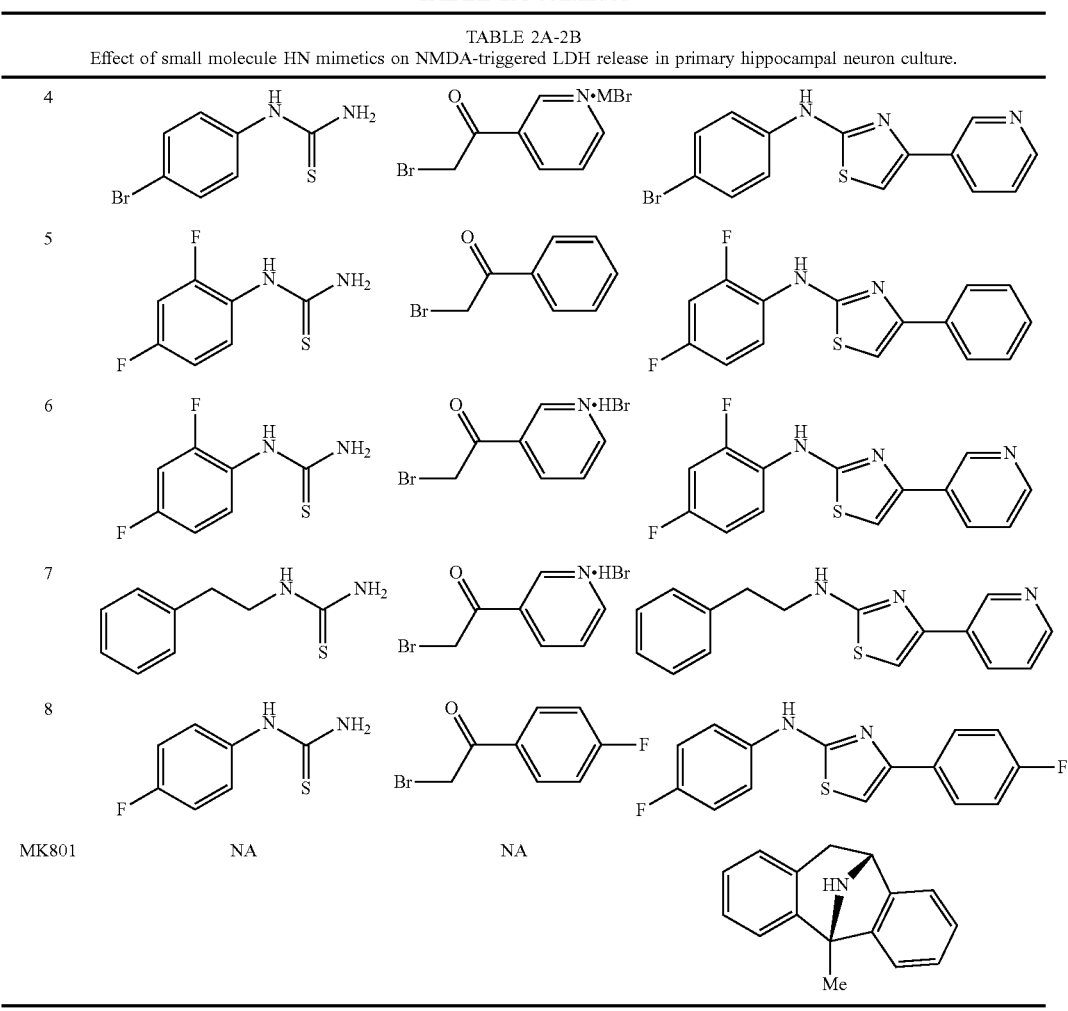

TABLE 2B

| Compound | MW | cLogP | TPSA | decrease in LDH release, % of control |
|---|---|---|---|---|
| RCGD423 (1) | 331.24 | 5.47 | 24.9 | 20 |
| 2 | 270.33 | 4.82 | 24.9 | 39 |
| 3 | 271.32 | 3.75 | 37.8 | 21 |
| 4 | 332.23 | 4.39 | 37.8 | 32 |
| 5 | 288.32 | 4.91 | 24.9 | 43 |
| 6 | 289.31 | 3.84 | 37.8 | 23 |
| 7 | 281.38 | 3.25 | 37.8 | 23 |
| 8 | 288.32 | 4.98 | 24.9 | 31 |
| MK801 | 337.37 | 3.48 | 12 | 43 |

TPSA: Total polar surface area

Referring to the compounds shown in Table 2, Compound 1 of Table 2 corresponds to structure PA1 in Table 1; Compound 2 of Table 2 corresponds to structure PA2 of Table 1; Compound 3 of Table 2 corresponds to structure PA3 of Table 1; Compound 4 of Table 2 corresponds to structure PA5 of Table 1; Compound 5 of Table 2 corresponds to structure PA6 of Table 1; Compound 6 of Table 2 corresponds to structure PA7 of Table 1; Compound 7 of Table 2 corresponds to structure 12 of Table 1; and Compound 8 of Table 2 corresponds to structure 14 of Table 1.

Example 4—Biological Evaluation

In order to identify further candidates as Gp130 agonist mimetic of TN that optionally protect neurons from amyloid-beta (Aβ) and excitotoxicity, flow chemistry can be utilized to efficiently generate analogs with greater potency, brain-penetrance, and oral availability. Candidates can be tested in the primary assay to determine Gp130 agonism as reflected by increases in pSTAT3 in vitro, in the secondary and tertiary assays for their ability to protect cells against amyloid-beta (Aβ) and NMDA-mediated toxicity. Analogs that meet criteria for advancement can then be tested in the Parallel Artificial Membrane Permeability Assay (PAMPA) and in Caco-2 cells for their potential to cross the blood-brain barrier (BBB). Finally, in vivo in pharmacokinetic studies can be performed to select compounds for further efficacy studies.

Example 5—Biological Studies

Figure 2:
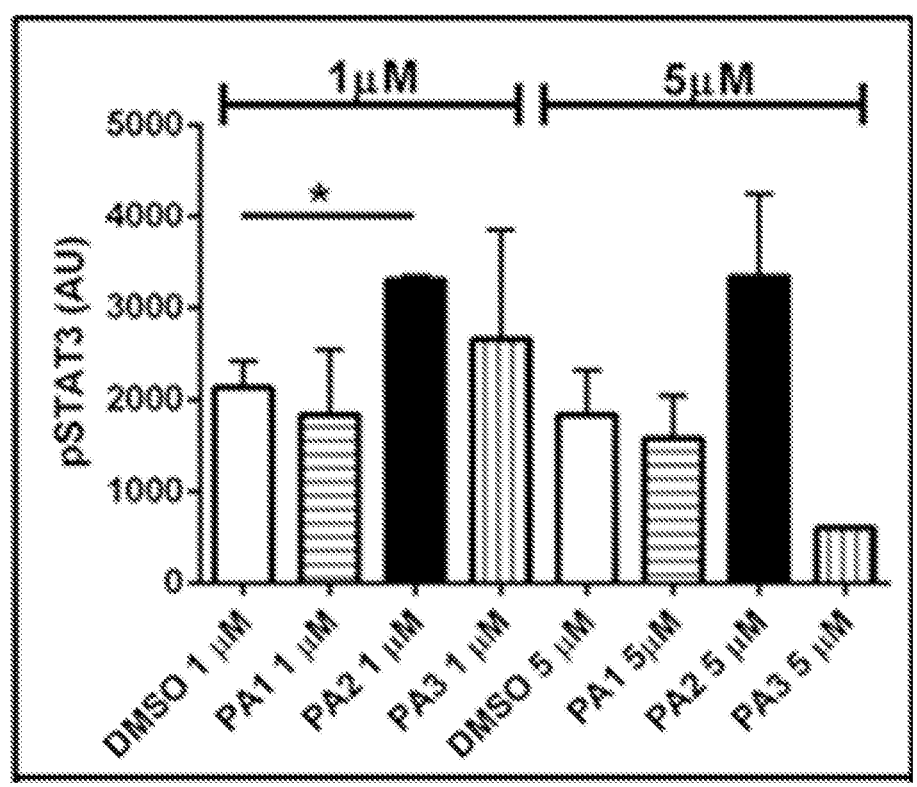
FIG. 2. Histogram of pSTAT3 levels (AU) as a function of compound or control levels in SH-SY5Y cells at 30-min exposure. Histogram bins (left to right): DMSO (1 μM), PA1 (1 μM), PA2 (1 μM), PA3 (1 μM), DMSO (5 μM), PA1 (5 μM), PA2 (5 μM), PA3 (5 μM).

Compounds that act as Gp130 agonists increase pSTAT3. Accordingly, the human neuroblastoma cell line SH-SY5Y was used, known to express the IL-6 receptor, which is the receptor for Gp130 to determine JAK-STAT activation as reflected by increases in pSTAT3. In the studies set forth in FIG. 2, cells were treated for 30 minutes with potential agonists PA1, PA2, and PA3; and then lysates were analyzed using the Sure-Fire Perkin-Elmer AlphaLISA for pTyr-STAT3. At both 1 µM and 5 M, PA2 increased pSTAT3 over the dimethyl sulfoxide (DMSO) control, suggesting that it can mimic HN activity.

In the present study, primary cultures of hippocampal neurons from E15-16 mouse embryos (C57BL/6) were used. The culture was made according to a previously described protocol with minor modifications [Bilousova et al. 2006, J. Neurochem. 97(1):44]. Hippocampi were isolated in ice-cold D-Hanks buffer containing (in mM: NaCl 136.7, KCl 5.4, NaHCO$_3$ 4.2, KH$_2$PO$_4$ 0.4, NaH$_2$PO$_4$ 0.6, glucose 5.6, and pH 7.4). In order to achieve a single cell suspension, hippocampal tissues were treated with papain (0.5 µg/mL) and Dnase (0.6 µg/mL) for 20 min at 37° C., followed by mechanical dissociation in complete media (Neurobasal medium supplemented with B27 (Invitrogen), 25 µM glutamate, and 1% penicillin-streptomycin). The cells were plated on poly-DL-ornithine (0.5 mg/mL), and laminin (5 µg/mL) pre-coated 96-well plates (Costar) at density 1×105 cells/mL and maintained in a humidified 5% CO2 incubator at 37° C. The proliferations of non-neuronal cells were limited by 48 h treatment with cytosine arabinoside (10 µM) started on first day in vitro (DIV1). All experiments were performed at 9 DIV cells.

Hippocampal neurons isolated from embryos were cultured for 8 days before treatment with chemical modulators (compounds). Neurons were either preincubated with compounds 1-8, HN, HNG, SC144 or MK801 for 16 h at 10 µM each; or vehicle-only (controls). After the preincubation with or without compounds 1-8, HN, HNG, SC144 and MK801, neurotoxicity was induced by the treatment with 100 µM NMDA and 10 µM glycine for 2.5 has described previously with some modification [Cui et al., 2014, Scientific World Journal, 341529]. Briefly, the cells were washed three times with prewarmed Locke's buffer containing (in mM: NaCl 154, KCl 5.6, NaHCO$_3$ 3.6, CaCl$_2$ 2.3, MgCl$_2$ 1.2, glucose 5.6, HEPES 5, and pH 7.4) to remove traces of growth medium. Neurons were incubated for 2.5 h with either compound-free or neurotoxin-containing Mg$^{2+}$ free Locke's buffer (NMDA, compounds 1-8, HN, HNG, SC144 and MK801 were added at concentrations as mentioned above). The incubation was terminated by removal of compound-containing buffer, followed by washing with prewarmed drug-free Locke's buffer containing 1 mM Mg$^{2+}$. After the last wash, cells were cultured in fresh culture medium with compounds 1-8, HN, HNG, SC144 and MK801 for 20 h at 10 µM each.

Assessment of cell damage was done by measuring the LDH activity in the culture medium. The experiment was performed per the manufacturer's protocol (Promega). Release LDH levels were expressed as a percentage compared with that of the DMSO control group (100%).

A highly lipophilic non-fluorescent and cell permeable compound, calcein-acetoxymethyl ester (calcein-AM) was used to determine cell viability. Calcein-AM can be converted by intracellular esterases into calcein, an anionic fluorescent form, only staining viable cells and provides both morphological and functional information of undamaged cells. The manufacturer's protocol was followed with some modification. Briefly, cells were washed once in Locke's buffer after NMDA exposure and loaded with 2 µM calcein-AM (ThermoFisher scientific) in Locke's buffer for 30 min, followed by a wash with warm Locke's buffer. Fluorescent images of live cells were collected using Lionheart FX automated digital microscope equipped with 4× objective and GFP filter cube (469/525); data was processed and analyzed using Gen5 software v. 3.00 (BioTek).

The brain penetrance and plasma levels of compound 2 were assessed in a pharmacokinetic (PK) study comprising oral dosing (30 mg/kg and 10 mg/kg) and subcutaneous (sub-Q, 10 mkd) injection. For each route and dose, 5 adult wildtype mice received either 5 µL of a 50 mg/ml stock in 100% DMSO mixed 50:50 with flavoring to give 10 µL total for 10 mg/kg oral; or 10 µL of a 75 mg/ml stock in 100% DMSO mixed 50:50 with flavoring to give 20 µL final for 30 mg/kg oral; or were injected with 50 µL of a 5 mg/ml stock in 100% DMSO for sub-Q 10 mg/kg, Mice were euthanized by ketamine/xylazine over-anesthesia at 1, 2, 4, 6, and 8 h post-dosing, and blood collected by cardiac puncture. The mice were then perfused with saline and brain tissue dissected and snap frozen on dry ice. Blood was centrifuged at 3000 rpm for 10 min and the plasma supernatant was collected. Both plasma and the right hemi-brain were sent to Integrated Analytical Solutions (IAS, Berkeley, Calif.) with a reference sample of compound for compound level analysis in tissue and plasma. The compound levels were determined using a LC-MS/MS approach.

Example 6—Molecular Modeling

Swiss Dock server [Grosdidier et al. 2011, Nucleic Acids Res., 39:W270] was used for the docking experiments between compounds 1-8, SC144 and the extracellular domains of Gp130. All rotatable single bonds were allowed to rotate in the ligand and the docking results were screened and analyzed with the Chimera program [Pettersen et al. 2004, J. Comput. Chem., 25(13):1605]. The ClusPro docking server was used to model the interactions between humanin and the extracellular domains of Gp130 [Comeau et al. 2004, Nucleic Acids Res., 32:W96]. The best-docked model was selected based on a balanced score that was dependent on the electrostatic, Van der Walls contacts and hydrophobic interactions as well as the shape complementarity score. The chosen model was further subjected to energy minimization with CHARMM to relieve steric clashes [Brooks et al. 2009, J. Comput. Chem., 30(10): 1545].

In view of the foregoing detailed description of preferred embodiments of the present disclosure, it readily will be understood by those persons skilled in the art that the present disclosure is susceptible to broad utility and application. While various aspects have been described in the context of screen shots, additional aspects, features, and methodologies of the present disclosure will be readily discernable therefrom. Many embodiments and adaptations of the present disclosure other than those herein described, as well as many variations, modifications, and equivalent arrangements and methodologies, will be apparent from or reasonably suggested by the present disclosure and the foregoing description thereof, without departing from the substance or scope of the present disclosure. Furthermore, any sequence(s) and/or temporal order of steps of various processes described and claimed herein are those considered to be the best mode contemplated for carrying out the present disclosure. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in various different sequences and orders, while still falling within the scope of the present inventions. In addition, some steps may be carried out simultaneously. Accordingly, while the present disclosure has been described herein in detail in relation to preferred embodiments, it is to be understood that this disclosure is only illustrative and exemplary of the present disclosure and is made merely for purposes of providing a full and enabling disclosure of the disclosure. The foregoing disclosure is not intended nor is to be construed to limit the present disclosure or otherwise to exclude any such other embodiments, adaptations, variations, modifications and equivalent arrangements, the present disclosure being limited only by the claims appended hereto and the equivalents thereof.

SEQUENCE LISTING
SEQ ID NO: 1
MLTLQTWLVQ ALFIFLTTES TGELLDPCGY ISPESPVVQL

HSNFTAVCVL KEKCMDYFHV NANYIVWKTN HFTIPKEQYT

IINRTASSVT FTDIASLNIQ LTCNILTFGQ LEQNVYGITI

ISGLPPEKPK NLSCIVNEGK KMRCEWDGGR ETHLETNFTL

KSEWATHKFA DCKAKRDTPT SCTVDYSTVY FVNIEVWVEA

ENALGKVTSD HINFDPVYKV KPNPPHNLSV INSEELSSIL

KLTWTNPSIK SVIILKYNIQ YRTKDASTWS QIPPEDTAST

RSSFTVQDLK PFTEYVFRIR CMKEDGKGYW SDWSEEASGI

TYEDRPSKAP SFWYKIDPSH TQGYRTVQLV WKTLPPFEAN

GKILDYEVTL TRWKSHLQNY TVNATKLTVN LTNDRYLATL

TVRNLVGKSD AAVLTIPACD FQATHPVMDL KAFPKDNMLW

VEWTTPRESV KKYILEWCVL SDKAPCITDW QQEDGTVHRT

YLRGNLAESK CYLITVTPVY ADGPGSPESI KAYLKQAPPS

KGPTVRTKKV GKNEAVLEWD QLPVDVQNGF IRNYTIFYRT

IIGNETAVNV DSSHTEYTLS SLTSDTLYMV RMAAYTDEGG

KDGPEFTFTT PKFAQGEIEA IVVPVCLAFL LTTLLGVLFC

FNKRDLIKKH IWPNVPDPSK SHIAQWSPHT PPRHNFNSKD

QMYSDGNFTD VSVVEIEAND KKPFPEDLKS LDLFKKEKIN

TEGHSSGIGG SSCMSSSRPS ISSSDENESS QNTSSTVQYS

TVVHSGYRHQ VPSVQVFSRS ESTQPLLDSE ERPEDLQLVD

HVDGGDGILP RQQYFKQNCS QHESSPDISH FERSKQVSSV

NEEDFVRLKQ QISDHISQSC GSGQMKMFQE VSAADAFGPG

TEGQVERFET VGMEAATDEG MPKSYLPQTV RQGGYMPQ

---

What is claimed is:

1. A method for treating Alzheimer's disease in a subject in need thereof, the method comprising administering to the subject an effective amount of a compound or a pharmaceutically acceptable salt thereof; wherein the compound is:

[chemical structure: 4-fluorophenyl-NH-thiazole-phenyl]

,

[chemical structure: 4-fluorophenyl-NH-thiazole-pyridin-3-yl]

, or

[chemical structure: 4-fluorophenyl-NH-thiazole-pyrimidin-5-yl]

.

2. The method of claim 1, wherein the compound is:

[chemical structure: 4-fluorophenyl-NH-thiazole-phenyl]

.

3. The method of claim 1, wherein the compound is:

[chemical structure: 4-fluorophenyl-NH-thiazole-pyrimidin-5-yl]

.

4. The method of claim 1, wherein the compound is:

[chemical structure: 4-fluorophenyl-NH-thiazole-pyridin-3-yl]

.

5. The method of claim 1, further comprising co-administering a different compound for treating Alzheimer's disease.

6. A method for treating Alzheimer's disease in a subject in need thereof, the method comprising administering to the subject an effective amount of a compound or a pharmaceutically acceptable salt thereof; wherein the compound is:

[chemical structure: 4-bromophenyl-NH-thiazole-phenyl]

,

[chemical structure: 4-fluorophenyl-NH-thiazole-phenyl]

,

-continued

[chemical structure: 4-fluorophenyl-NH-thiazole-pyridin-3-yl]

,

[chemical structure: 4-fluorophenyl-NH-thiazole-pyrimidin-5-yl]

,

[chemical structure: 4-bromophenyl-NH-thiazole-pyridin-3-yl]

,

[chemical structure: 2,4-difluorophenyl-NH-thiazole-phenyl]

,

[chemical structure: 2,4-difluorophenyl-NH-thiazole-pyridin-3-yl]

,

[chemical structure: 4-bromophenyl-NH-thiazole-(4-fluorophenyl)]

,

[chemical structure: 2,4-difluorophenyl-NH-thiazole-(2,4-difluorophenyl)]

,

[chemical structure: 2,4-difluorophenyl-NH-thiazole-phenyl]

,

[chemical structure: phenethyl-NH-thiazole-phenyl]

,

[chemical structure: phenethyl-NH-thiazole-pyridin-3-yl]

,

[chemical structure: 4-fluorophenyl-NH-thiazole-(2,4-difluorophenyl)]

,

[chemical structure: 4-fluorophenyl-NH-thiazole-(4-fluorophenyl)]

,

[chemical structure: 4-bromophenyl-NH-oxazole-phenyl]

,

-continued
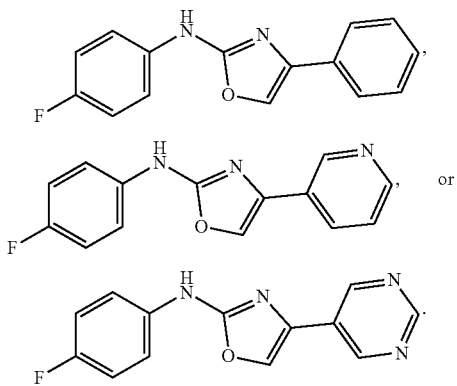
7. The method of claim 6, wherein the compound is:
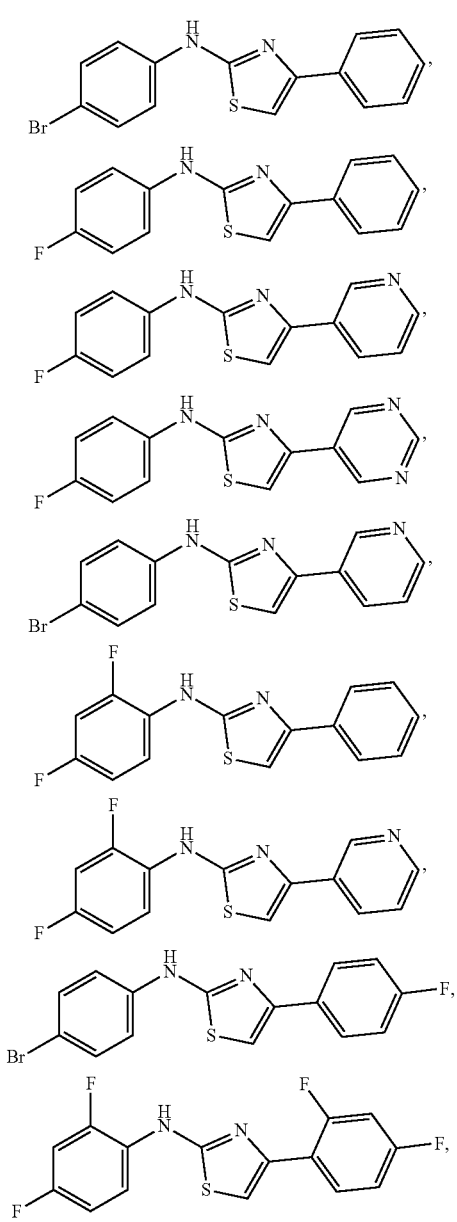
-continued
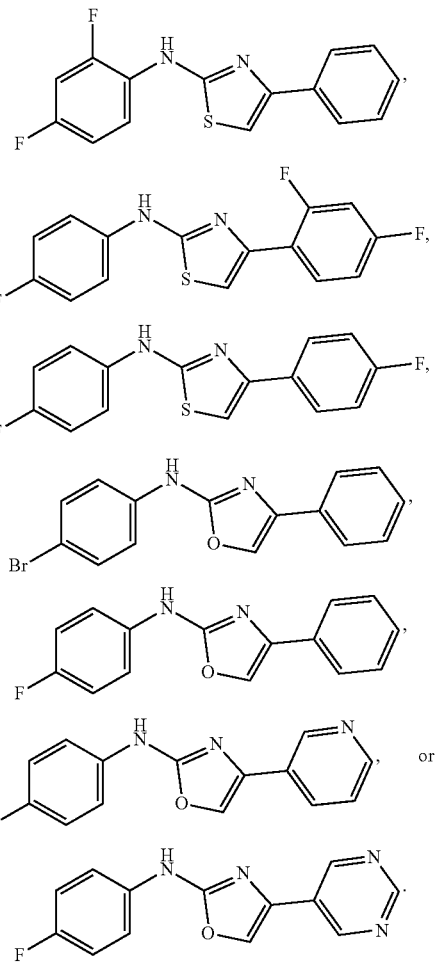
8. The method of claim 6, wherein the compound is:
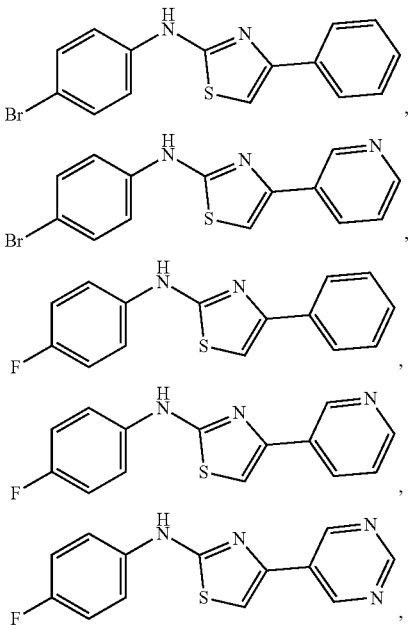

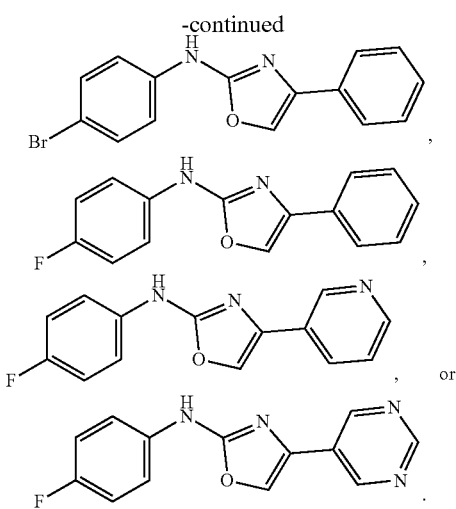

9. The method of claim 6, further comprising co-administering a different compound for treating Alzheimer's disease.

10. A method for treating Alzheimer's disease in a subject in need thereof, the method comprising administering to the subject an effective amount of a compound of Formula (A) or a pharmaceutically acceptable salt thereof; wherein the compound of Formula (A) is:

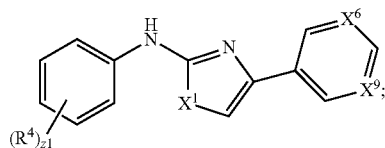

wherein:
$X^1$ is oxygen or sulfur;
$X^6$ and $X^9$ are each independently CH or N;
$R^4$ is halogen; and
z1 is an integer from 0 to 5.

11. The method of claim 10, wherein $R^4$ is independently fluorine, bromine, or chlorine.

12. The method of claim 10, wherein $R^4$ is independently fluorine or bromine.

13. The method of claim 10, wherein $R^4$ is fluorine.

14. The method of claim 10, wherein $R^4$ is bromine.

15. The method of claim 10, wherein z1 is 0.

16. The method of claim 10, wherein z1 is 1.

17. The method of claim 10, further comprising co-administering a different compound for treating Alzheimer's disease.

* * * * *

SEQUENCE LISTING

<160> NUMBER OF SEQ ID NOS: 1

<210> SEQ ID NO 1
<211> LENGTH: 918
<212> TYPE: PRT
<213> ORGANISM: Homo sapiens

<400> SEQUENCE: 1

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys

-continued

```
            130                 135                 140
Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
    370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
    530                 535                 540

Asp Val Gln Asn Gly Phe Ile Arg Asn Tyr Thr Ile Phe Tyr Arg Thr
545                 550                 555                 560
```

```
Ile Ile Gly Asn Glu Thr Ala Val Asn Val Asp Ser His Thr Glu
            565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
            610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
            645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
            675                 680                 685

Thr Asp Val Ser Val Val Glu Ile Glu Ala Asn Asp Lys Lys Pro Phe
            690                 695                 700

Pro Glu Asp Leu Lys Ser Leu Asp Leu Phe Lys Glu Lys Ile Asn
705                 710                 715                 720

Thr Glu Gly His Ser Ser Gly Ile Gly Gly Ser Ser Cys Met Ser Ser
            725                 730                 735

Ser Arg Pro Ser Ile Ser Ser Ser Asp Glu Asn Glu Ser Gln Asn
            740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
            770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
            805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
            850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
            885                 890                 895

Thr Asp Glu Gly Met Pro Lys Ser Tyr Leu Pro Gln Thr Val Arg Gln
            900                 905                 910

Gly Gly Tyr Met Pro Gln
            915
```